US011268954B2

(12) United States Patent
Sato et al.

(10) Patent No.: US 11,268,954 B2
(45) Date of Patent: *Mar. 8, 2022

(54) IMMUNOASSAY APPARATUS

(71) Applicant: SYSMEX CORPORATION, Kobe (JP)

(72) Inventors: Toshiyuki Sato, Kobe (JP); Toshikatsu Fukuju, Kobe (JP); Shuhei Kaneko, Kobe (JP); Atsushi Aoki, Kobe (JP); Tomohiro Okuzaki, Kobe (JP); Yasuhiro Takeuchi, Kobe (JP); Yutaka Kawamoto, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/862,999

(22) Filed: Apr. 30, 2020

(65) Prior Publication Data

US 2020/0256868 A1 Aug. 13, 2020

Related U.S. Application Data

(63) Continuation of application No. 15/719,642, filed on Sep. 29, 2017, now Pat. No. 10,648,973, which is a
(Continued)

(30) Foreign Application Priority Data

Mar. 31, 2015 (JP) .................................. 2015-070834

(51) Int. Cl.
*G01N 33/543* (2006.01)
*G01N 35/10* (2006.01)
(Continued)

(52) U.S. Cl.
CPC ..... *G01N 33/54386* (2013.01); *G01N 33/543* (2013.01); *G01N 33/5764* (2013.01);
(Continued)

(58) Field of Classification Search
CPC combination set(s) only.
See application file for complete search history.

(56) References Cited

U.S. PATENT DOCUMENTS 5,324,635 A * 6/1994 Kawase ............. G01N 21/6428
250/459.1
5,332,679 A * 7/1994 Simons ............. G01N 33/54306
435/7.5

(Continued)

FOREIGN PATENT DOCUMENTS

CN 1694725 A 11/2005
CN 101324631 A 12/2008
(Continued)

OTHER PUBLICATIONS

Office Action (JPOA) dated Dec. 8, 2020 in a counterpart Japanese patent application.
(Continued)

*Primary Examiner* — Brian R Gordon
(74) *Attorney, Agent, or Firm* — Metrolex IP Law Group, PLLC

(57) ABSTRACT

An immunoassay apparatus may include: a sample dispenser part that dispenses a sample into a first reaction container; a reagent dispenser part that dispenses, into the first reaction container: a solid-phase reagent containing a solid-phase carrier; a labeled reagent; and a releasing reagent that releases, from the solid-phase carrier, an immune complex including a target substance and a labeled substance; a measurement part that measures a signal based on the labeled substance in the immune complex in a second
(Continued)

reaction container; a container supply part that stores a plurality of reaction containers; a transfer part that transfers the first reaction container so that the sample dispenser part and the reagent dispenser part perform a dispensing operation to the first reaction container, and that transfers the second reaction container so that the immune complex dispended from the first reaction container is dispensed into the second container.

9 Claims, 13 Drawing Sheets

Related U.S. Application Data continuation of application No. PCT/JP2016/060833, filed on Mar. 31, 2016.

(51) Int. Cl.
   *G01N 35/02* (2006.01)
   *G01N 33/576* (2006.01)
(52) U.S. Cl.
   CPC .......... *G01N 35/025* (2013.01); *G01N 35/10* (2013.01); *G01N 35/1002* (2013.01); *G01N 2035/103* (2013.01)

(56) References Cited

U.S. PATENT DOCUMENTS

| | | | | |
|---|---|---|---|---|
| 5,882,594 | A * | 3/1999 | Kawaguchi | G01N 35/025 422/64 |
| 9,229,018 | B2 * | 1/2016 | Toyoshima | G01N 35/1002 |
| 9,304,140 | B2 * | 4/2016 | Wakamiya | G01N 35/0092 |
| 2006/0204997 | A1 * | 9/2006 | Macioszek | G01N 35/0099 435/6.11 |
| 2007/0148042 | A1 * | 6/2007 | Ootani | G01N 35/10 422/63 |
| 2007/0172390 | A1 * | 7/2007 | Ootani | G01N 35/0099 422/64 |
| 2010/0075407 | A1 * | 3/2010 | Duffy | G01N 33/54313 435/287.2 |
| 2010/0107744 | A1 * | 5/2010 | Fukuda | G01N 35/1065 73/64.56 |
| 2011/0129815 | A1 * | 6/2011 | Yamagaito | G01N 33/5767 435/5 |
| 2012/0087830 | A1 * | 4/2012 | Wakamiya | G01N 35/025 422/67 |
| 2012/0149127 | A1 * | 6/2012 | Toyoshima | G01N 35/0098 436/177 |
| 2015/0330982 | A1 | 11/2015 | Yamagaito et al. | |
| 2016/0282374 | A1 * | 9/2016 | Barnett | G01N 1/30 |
| 2016/0282376 | A1 * | 9/2016 | Keller | G01N 35/00722 |

FOREIGN PATENT DOCUMENTS

| | | |
|---|---|---|
| CN | 101393225 A | 3/2009 |
| CN | 101393227 A | 3/2009 |
| CN | 102081018 A | 6/2011 |
| CN | 102207510 A | 10/2011 |
| CN | 102246043 A | 11/2011 |
| CN | 102539800 A | 7/2012 |
| CN | 103217536 A | 7/2013 |
| JP | H11-125634 A | 5/1999 |
| JP | 2000-105236 A | 4/2000 |
| JP | 2012-083227 A | 4/2012 |
| WO | 03/012395 A2 | 2/2003 |
| WO | 2014115878 A1 | 7/2014 |

OTHER PUBLICATIONS

Office Action (CNOA) dated Oct. 11, 2021 in a counterpart Chinese patent application.

* cited by examiner

IMMUNOASSAY APPARATUS

CROSS REFERENCE TO RELATED APPLICATIONS

This application is a continuation of application Ser. No. 15/719,642, filed on Sep. 29, 2017 and patented as U.S. Pat. No. 10,648,973 on May 12, 2020, which is a continuation application of International Application No. PCT/JP2016/060833, filed on Mar. 31, 2016, which claims priority based on the Article 8 of Patent Cooperation Treaty from prior Japanese Patent Application No. 2015-070834, filed on Mar. 31, 2015 and patented as Japanese Patent No. 6,166,008 on Jul. 26, 2017, the entire contents of all of which are incorporated herein by reference.

BACKGROUND

There is an immunoassay apparatus that performs measurement on a test substance using an antigen-antibody reaction. As a technique of enhancing sensitivity of the measurement by the immunoassay apparatus, there is an immune complex transfer method (see, for example, Japanese Patent Application Publication No. H01-254868 (Patent Literature 1)).

In the above technique disclosed in Patent Literature 1, an immune complex of the test substance and a labeled antibody is generated on a carrier using the antigen-antibody reaction. After a releasing reagent is input to a measurement specimen including a conjugate of the immune complex and the carrier, the immune complex released from the carrier is extracted from the measurement specimen (a procedure 1). With a procedure 1, the labeled antibody nonspecifically adsorbed by the carrier is removed. Subsequently, immune complex measurement is performed using the extracted immune complex (a procedure 2).

In the immunoassay performed using the immune complex transfer method, a pretreatment apparatus that carries out the procedure 1 and an immunoassay apparatus that carries out the procedure 2 need to be separately used. There is a need for a single apparatus capable of performing the immunoassay.

SUMMARY

One or more aspects may be directed to enable a single apparatus to perform high-sensitivity immunoassay using the immune complex transfer method.

An immunoassay apparatus according to a first aspect may include: a sample dispenser part that dispenses a sample into a first reaction container; a reagent dispenser part that dispenses, into the first reaction container: a solid-phase reagent containing a solid-phase carrier; a labeled reagent containing a labeled substance; and a releasing reagent that releases, from the solid-phase carrier, an immune complex including a target substance included in the sample and the labeled substance; a measurement part that measures a signal based on the labeled substance included in the immune complex in a second reaction container; a container supply part that stores a plurality of reaction containers including the first reaction container and the second reaction container; a transfer part that transfers the first reaction container supplied from the container supply part so that the sample dispenser part and the reagent dispenser part perform a dispensing operation to the first reaction container, and that transfers the second reaction container supplied from the container supply part so that the immune complex dispended from the first reaction container is dispensed into the second container.

An immunoassay apparatus according to a second aspect may include: a sample dispenser part that dispenses a sample into a first reaction container; a reagent dispenser part that: dispenses, into the first reaction container: a first solid-phase reagent containing a first solid-phase carrier; a labeled reagent containing a labeled substance; and a releasing reagent that releases, from the first solid-phase carrier, an immune complex including a target substance included in the sample and the labeled substance; and dispenses, into a second reaction container storing the immune complex dispensed from the first reaction container, the second solid-phase reagent containing a second solid-phase carrier, a BF separation part that performs separation processing for the immune complex in the first reaction container storing the dispensed first solid-phase reagent and separation processing for the immune complex in the second reaction container storing the dispensed second solid-phase reagent; a measurement part that measures a signal based on the labeled substance included in the immune complex in the second reaction container.

According to one or more aspects, it may be possible to perform, with one apparatus, high-sensitivity immunoassay using the immune complex transfer method.

DETAILED DESCRIPTION

Figure 1:
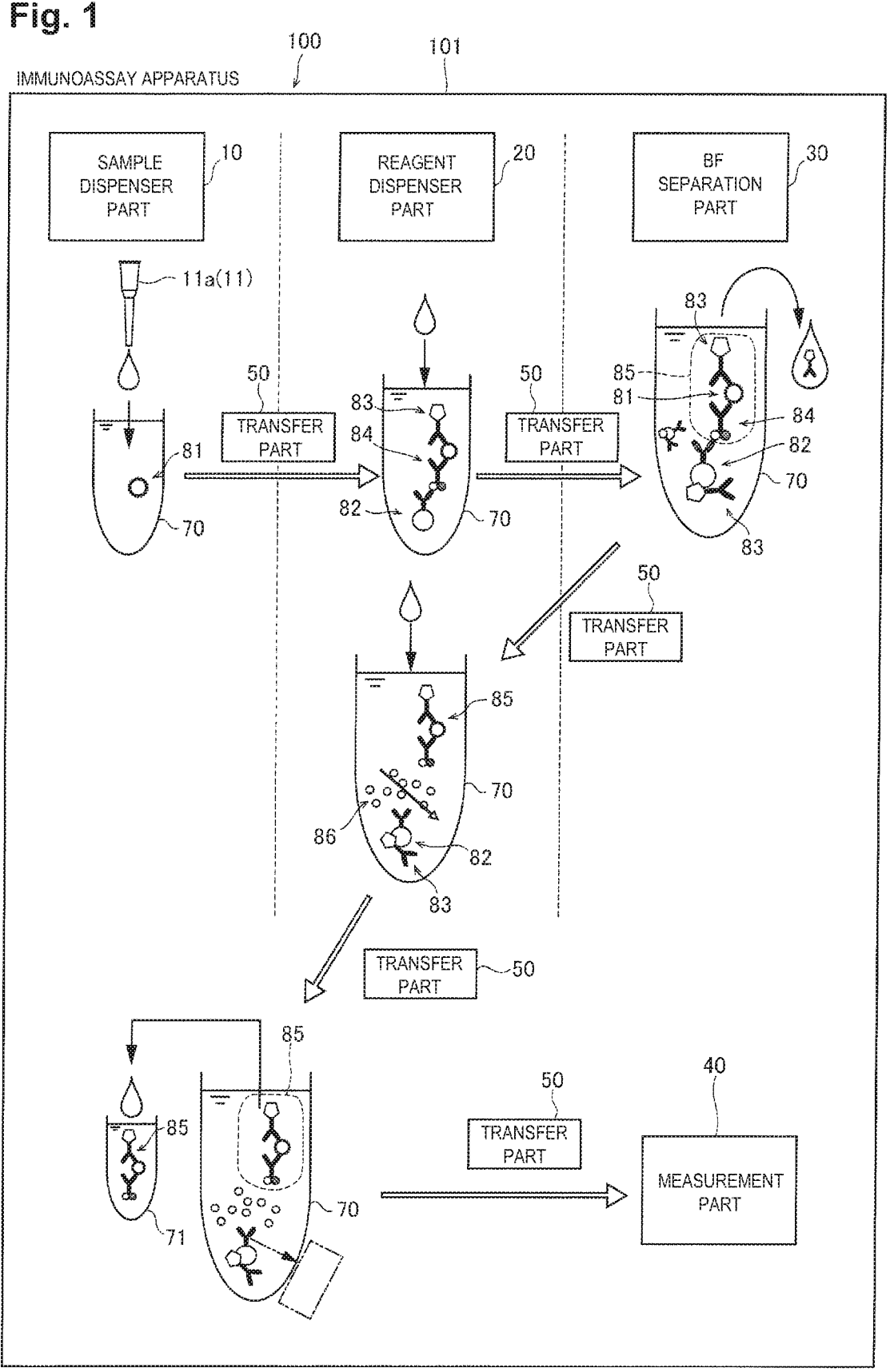
FIG. 1 is a diagram illustrating an overview of an immunoassay apparatus according to an embodiment.

Embodiments are explained below with reference to the drawing.

[Overview of an Immunoassay Apparatus]

First, an overview of immunoassay apparatus 100 according to an embodiment is explained with reference to FIG. 1

Immunoassay apparatus 100 measures a target substance in a sample using the antigen-antibody reaction. The target substance is, for example, an antigen or an antibody, protein, peptide, or the like included in blood. Immunoassay apparatus 100 acquires a serum as a sample and performs quantitative measurement or qualitative measurement of an antigen, antibody, or the like included in the sample. The sample may be plasma. Note that the antigen-antibody reaction includes not only a reaction of the antigen and the antibody but also a reaction caused by a specific binding substance such as aptamer. The aptamer is a nucleic acid or peptide synthesized to be specifically bound with a specific substance.

In this embodiment, immunoassay apparatus 100 performs separation processing for an immune complex by the immune complex transfer method. The immune complex transfer method is a method of forming, on a solid-phase carrier, an immune complex (a bound body by the antigen-antibody reaction) including a target substance and a labeled substance and thereafter dissociating the immune complex and the solid-phase carrier and separating the dissociated immune complex from the solid-phase carrier. Consequently, an unnecessary labeled substance nonspecifically bound with the solid-phase carrier in a process for forming the immune complex on the solid-phase carrier is separated from the immune complex together with the solid-phase carrier. As a result, compared with a case of performing measurement without performing the immune complex transfer method, it is possible to reduce a noise level. Therefore, it is possible to reduce a baseline of measurement data and increase sensitivity of immune measurement.

As illustrated in FIG. 1, immunoassay apparatus 100 includes sample dispenser part 10, reagent dispenser part 20, BF separation part 30, measurement part 40, and transfer part 50. The parts are housed in housing 101 of immunoassay apparatus 100.

Sample dispenser part 10 can dispense a sample including target substance 81 into first reaction container 70. Sample dispenser part 10 aspirates the sample from a test tube (not illustrated) in which the sample is stored and dispenses a predetermined amount of the sample into first reaction container 70.

Sample dispenser part 10 is capable of detachably attaching, for example, dispensing tip 11 to the end of sample dispenser part 10. Dispensing tip 11 is, for example, a disposable hollow cylindrical distal end component capable of storing a predetermined amount of a sample. In this case, sample dispenser part 10 dispenses the sample into first reaction container 70 via first dispensing tip 11a. By aspirating the sample via dispensing tip 11 and storing the sample in dispensing tip 11 and discharging the sample to a desired container, it is possible to bring only dispensing tip 11 into contact with the sample and dispense the sample.

Reagent dispenser part 20 can dispense various reagents used for immunoassay. Specifically, reagent dispenser part 20 dispenses a solid-phase reagent containing solid-phase carrier 82 and a labeled reagent containing labeled substance 83 into first reaction container 70 which stores the sample dispensed. The various reagents dispensed by reagent dispenser part 20 are liquid reagents and stored in separate reagent containers of the respective types. The solid-phase reagent is a liquid reagent containing a solid-phase carrier in liquid. The labeled reagent is a liquid reagent containing a labeled substance in liquid.

Solid-phase carrier 82 is, for example, a publicly-known particle used in the immunoassay. Examples of the particle include a magnetic particle, a latex particle, a red blood cell, and a gelatin particle. For separation processing by BF separation part 30, it may be preferable to use the magnetic particle as solid-phase carrier 82. The magnetic particle only has to be a particle including a material having magnetism as a base material and used for normal immunoassay. For example, as the base material, magnetic particles obtained by using $Fe_2O_3$ and/or $Fe_3O_4$, cobalt, nickel, ferrite, and magnetite can be used. Solid-phase carrier 82 may be coated with a binding substance for binding solid-phase carrier 82 with target substance 81 or may be bound with target substance 81 via capturing substance 84 for binding solid-phase carrier 82 and target substance 81. Capturing substance 84 is an antigen, an antibody, or the like to be bound with solid-phase carrier 82 and with target substance 81. In this case, a reagent containing capturing substance 84 is dispensed into first reaction container 70 by reagent dispenser part 20.

Labeled substance 83 contains a label that is measurable by measurement part 40, and is to be bound with target substance 81 by the antigen-antibody reaction. Labeled substance 83 is not particularly limited as long as labeled substance 83 is an antibody including a publicly-known label using in the immunoassay. In a case where capturing substance 84 is used, labeled substance 83 may be bound with capturing substance 84. Examples of the label included in labeled substance 83 include an enzyme, a fluorescent substance, and a radioactive isotope. Examples of the enzyme include alkaline phosphatase (ALP), peroxidase, glucose oxidase, tyrosinase, and acid phosphatase. As the fluorescent material, fluoresceinisothiocyanate (FITC), green fluorescent protein (GFP), luciferin, and the like can be used. As the radioactive isotope, 125I, 14C, 32P, and the like can be used. As the label used in labeled substance 83 in this embodiment, an enzyme may be preferable.

In a case where the label is the enzyme, as a substrate for the enzyme of labeled substance 83, a publicly-known substrate only has to be selected as appropriate according to an enzyme in use. For example, as a substrate in the case in which the alkaline phosphatase is used as the enzyme, chemical light emitting substrates such as CDP-Star (registered trademark), (4-chloro-3-(methoxyspiro[1,2-dioxetane-3,2'-(5'-chloro)tricycle[3.3.1.13,7]decane]-4-yl)disodium phenylphosphate, CSPD (registered trademark), and (3-(4-methoxyspiro[1,2-dioxetane-3,2-(5'-chloro)tricycle [3.3.1.13,7]decane]-4-yl)disodium phenylphosphate), light emitting substrates such as p-nitrophenylphosphate, 5-bromo-4-chloro-3-indolyl phosphate (BCIP), 4-nitro blue tetrazolium (NBT), and iodonitroterazolium (INT), fluorescent substrates such as 4-methylumbelliferyl phosphate (4MUP), color development substrates such as 5-bromo-4-chloro-3-indolyl phosphate (BCIP), 5-bromo-6-chloro-disodium indolyl phosphate, and p-nitrophenylphosphorus can be used.

Reagent dispenser part 20 can include one or more reagent dispenser units according to types of reagents in use. The reagent dispenser unit of reagent dispenser part 20 performs dispensing of a reagent, for example, via a fixed aspiration tube. Reagent dispenser part 20 may use detachably attached dispensing tips.

In this embodiment, separation processing for an immune complex by the immune complex transfer method is performed by immunoassay apparatus 100.

Reagent dispenser part 20 dispenses, into first reaction container 70 which stores the sample dispensed, releasing reagent 86 with which immune complex 85 including target substance 81 and labeled substance 83 formed on solid-phase carrier 82 is released from solid-phase carrier 82. Releasing reagent 86 is selected as appropriate according to a type of binding of solid-phase carrier 82 and immune complex 85. Releasing reagent 86 is dispensed, whereby immune complex 85 is dissociated from solid-phase carrier 82 with which labeled substance 83 is nonspecifically bound other than immune complex 85.

Immune complex 85 released from solid-phase carrier 82 by releasing reagent 86 is dispensed into second reaction container 71. Consequently, immune complex 85 is separated and extracted from first reaction container 70 including solid-phase carrier 82, with which labeled substance 83 is nonspecifically bound, and transferred to another second reaction container 71. Immune complex 85 is transferred from first reaction container 70 to second reaction container 71, whereby immune complex 85 is separated from other unnecessary components adhering to a wall surface of first reaction container 70. The unnecessary components indicate all substances present in a container and unnecessary for measurement of target substance 81. The unnecessary components are, for example, components other than target substance 81 included in the sample, unreacted labeled substance 83 or the like not bound with target substance 81, and the like.

First reaction container 70 and second reaction container 71 are, for example, disposable containers made of resin. In this case, first reaction container 70 after the transfer of immune complex 85 to second reaction container 71 can be directly discarded. First reaction container 70 and second reaction container 71 may be common containers. That is, of two disposable containers of the same type, one disposable container may be used as first reaction container 70 and the other disposable container may be used as second reaction container 71. In this case, it is unnecessary to separately retain and store first reaction container 70 and second reaction container 71.

Aspiration of immune complex 85 can be realized by collecting solid-phase carrier 82 in first reaction container 70 and aspirating supernatant liquid in first reaction container 70. In a case where solid-phase carrier 82 is a magnetic particle, solid-phase carrier 82 can be collected in first reaction container 70 by a magnet. Consequently, it is possible to efficiently separate solid-phase carrier 82 and immune complex 85. In a case where solid-phase carrier 82 is a nonmagnetic bead, centrifugal separation may be performed or solid-phase carrier 82 may be naturally precipitated.

BF separation part 30 performs BF separation processing of separating solid-phase carrier 82, on which immune complex 85 including target substance 81 and labeled substance 83 is formed and a liquid component. After a sample, a solid-phase reagent, and a labeled reagent are dispensed, BF separation part 30 performs the BF separation processing before releasing reagent 86 is dispensed.

BF separation part 30 collects solid-phase carrier 82 bound with immune complex 85 in first reaction container 70 and aspirates a liquid component in first reaction container 70 to thereby remove the liquid component. In a case where solid-phase carrier 82 is the magnetic particle, BF separation part 30 removes the liquid component in first reaction container 70 while collecting, with the magnet, solid-phase carrier 82 bound with immune complex 85 in first reaction container 70. In a case where solid-phase carrier 82 is the nonmagnetic bead, BF separation part 30 removes the liquid component in first reaction container 70 by collecting solid-phase carrier 82 bound with immune complex 85 through centrifugal separation, natural precipitation, or the like and aspirating the supernatant liquid. After removing the liquid component in first reaction container 70, BF separation part 30 supplies cleaning liquid into first reaction container 70 and removes the liquid component again. BF separation part 30 performs the removal of the liquid component and the supply of the cleaning liquid one or more times.

BF separation part 30 may further perform separation processing on solid-phase carrier 82 bound with immune complex 85 in second reaction container 71. In this case, BF separation part 30 bounds immune complex 85 transferred to second reaction container 71 with another solid-phase carrier and removes, with the BF separation processing, unnecessary components from a specimen including immune complex 85 bound with the other solid-phase carrier. The unnecessary components in this case are, for example, a part of substances included in the supernatant liquid together with immune complex 85 among substances such as unreacted labeled substance 83 and releasing reagent 86 not bound with target substance 81.

Measurement part 40 is configured to measure a signal based on a label included in immune complex 85 dispensed into second reaction container 71. The measurement only has to be performed by an appropriate method corresponding to a type of a label used in labeled substance 83. A measurement method is not particularly limited. For example, in a case where the label used in labeled substance 83 is an enzyme, the measurement can be performed by measuring light, a color, and the like generated by causing a substrate to react with the enzyme. As the measurement part 40 in this case, a spectrophotometer, a luminometer, and the like can be used. In a case where labeled substance 83 is the radioactive isotope, a scintillation counter or the like can be used as measurement part 40.

Transfer part 50 is configured to transfer first reaction container 70 to a position where sample dispenser part 10 can perform dispensing, a position where reagent dispenser part 20 can perform dispensing, and BF separation part 30. Transfer part 50 includes one or more container transfer units. The container transfer unit is, for example, a catcher unit capable of gripping and transferring first reaction containers 70 one by one or a movable reaction-container holding part capable of moving while holding first reaction containers 70. Transfer part 50 can transfer second reaction container 71 to measurement part 40.

As explained above, in this embodiment, dispensing of releasing reagent 86 for the immune complex transfer method can be performed by reagent dispenser part 20 that dispenses a solid-phase reagent and a labeled reagent for immune chemical measurement. Dispensing of immune complex 85 for the immune complex transfer method can also be performed. Consequently, it is possible to carry out, with one immunoassay apparatus 100, high-sensitivity immunoassay in which the immune complex transfer method is used. Since immune complex 85 aspirated from first reaction container 70 is dispensed into separate second reaction container 71, it is possible to prevent carryover of unreacted labeled substance 83, releasing reagent 86, and the like adhering to first reaction container 70.

Specific Configuration Example of the Immunoassay Apparatus

In the following explanation, a specific configuration example of immunoassay apparatus 100 is explained in detail. The parts of immunoassay apparatus 100 explained above are specifically realized by a configuration illustrated in FIG. 2. The immunoassay apparatus 100 can perform the immune chemical measurement in which the immune complex transfer method is not carried out and high-sensitivity immunoassay in which the immune chemical measurement is used. In an example illustrated in FIG. 2, first test processing of performing the high-sensitivity immunoassay in which the immune complex transfer method is used and second test processing of performing the immune chemical measurement in which the immune complex transfer method is not carried out are performed concurrently. Note that reagents used in the first test processing are represented by R1 to R9. Reagents used in the second test processing are represented by r1 to r5.

Figure 2:
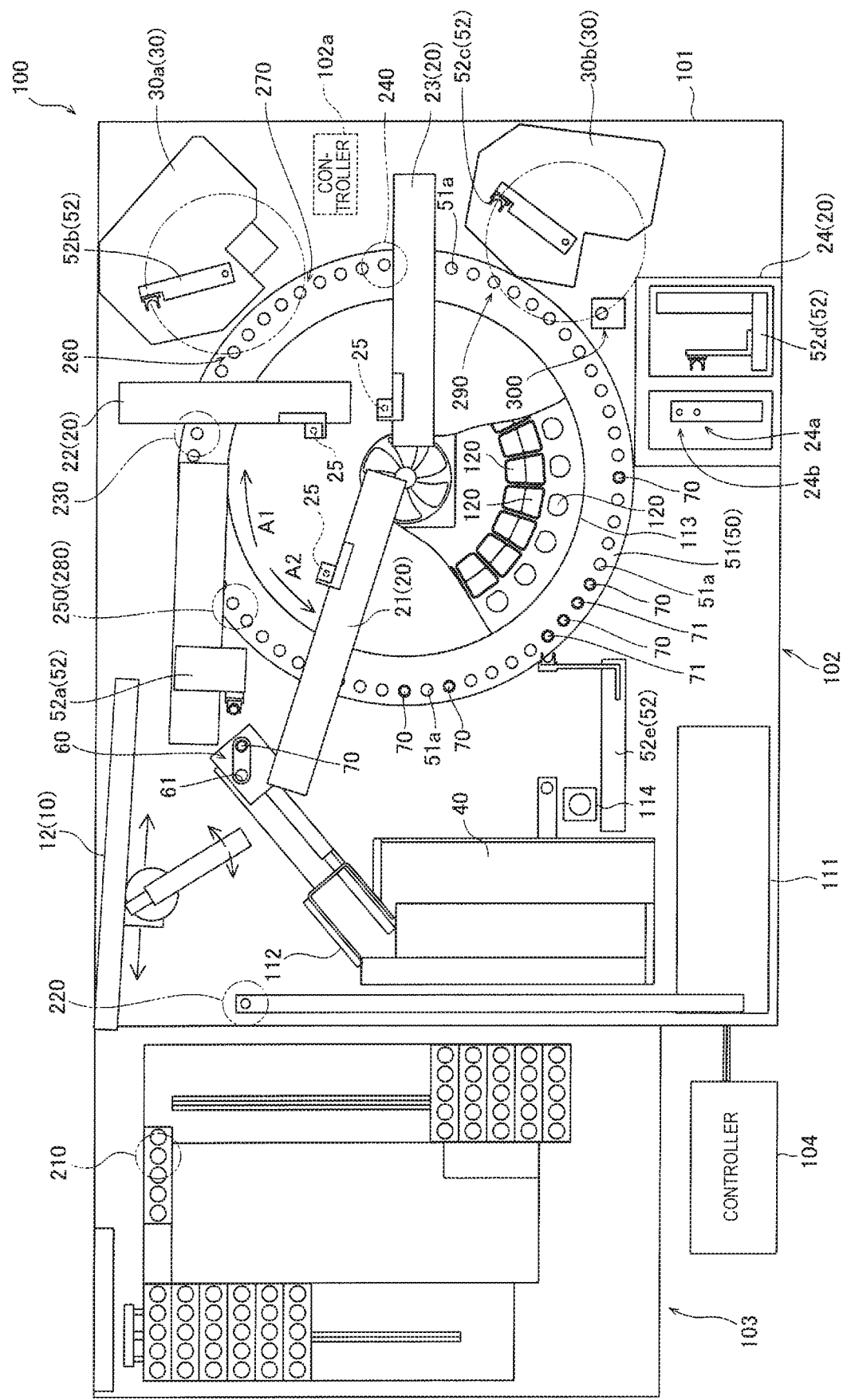
FIG. 2 is a plan view illustrating an overall configuration example of an immunoassay apparatus according to an embodiment.

In the configuration example illustrated in FIG. 2, immunoassay apparatus 100 includes measurement mechanism part 102, sample conveyance part 103 disposed adjacent to measurement mechanism part 102, and controller 104 including a PC (personal computer) electrically connected to measurement mechanism part 102.

Sample conveyance part 103 is capable of conveying a rack on which test tubes, each of which stores a sample, are placed. Sample conveyance part 103 can convey the test tube, which stores a sample, to sample aspiration position 210 for dispenser part 10 explained below.

Controller 104 is a computer including a CPU, a display part, an input part, and a storage part. The CPU analyzes a measurement result obtained by measurement mechanism part 102 and displays a result of the analysis on the display part. The storage part includes a HDD (hard disk drive) and stores various kinds of computer programs, data of measurement results, and the like.

In measurement mechanism part 102, sample dispenser part 10, reagent dispenser part 20, BF separation part 30, measurement part 40, and transfer part 50 are provided. The parts in measurement mechanism part 102 are controlled by controller 102*a* provided in measurement mechanism part 102. In controller 102*a*, a substrate mounted with an FPGA and the like is used. Controller 102*a* is communicably connected to sample conveyance part 103 and controller 104. Controller 102*a* performs transmission of measurement result data to controller 104, transmission of an operation command to sample conveyance part 103, and the like.

In the configuration example illustrated in FIG. 2, controller 104 controls first test processing. The first test processing includes: first solid phasing processing of binding target substance 81, labeled substance 83, and first solid-phase carrier 82*a*; releasing processing of releasing immune complex 85 from first solid-phase carrier 82*a*; second solid phasing processing of binding immune complex 85 and second solid-phase carrier 82*b*; and measurement processing of measuring a signal. That is, controller 104 controls the first test processing of performing the high-sensitivity immunoassay in which the immune complex transfer method is used. Consequently, it is possible to perform, with one immunoassay apparatus 100, the high-sensitivity immunoassay in which the immune complex transfer method is used. Note that "controlling" includes causing, by controller 104, the immunoassay apparatus 100 to perform the various kinds of processes in the first test processing.

In the configuration example illustrated in FIG. 2, controller 104 allocates first reaction container 70 and second reaction container 71 to the first detection processing for a measurement order. Specifically, before completion of the releasing processing, controller 104 allocates second reaction container 71 to the first test processing. Note that "before completion of the releasing processing" is, for example, before a start of second BF separation processing (explained below) for performing dispensing into second reaction container 71 which stores releasing reagent 86 dispensed. "Allocating first reaction container 70 and second reaction container 71" includes at least one of recording information for using first reaction container 70 and second reaction container 71 in the storage part and supplying first reaction container 70 and second reaction container 71 to reaction-container holding part 60. Consequently, in the high-sensitivity immunoassay in which the immune complex transfer method is used, it is possible to surely prepare two reaction containers (first reaction container 70 and second reaction container 71). Since second reaction container 71 is allocated before the completion of the releasing processing, it is possible to suppress a delay in the allocation of second reaction container 71. As a result, it is possible to suppress a delay in the measurement processing.

In the configuration example illustrated in FIG. 2, in the first solid phasing processing, controller 104 controls the first test processing so as to perform first solid-phase carrier binding processing after labeled substance binding processing. Note that the labeled substance binding processing is processing of binding target substance 81 and labeled substance 83. The first solid-phase carrier binding processing is processing of binding immune complex 85 including target substance 81 and labeled substance 83 and first solid-phase carrier 82*a*. Consequently, since immune complex 85 including target substance 81 and labeled substance 83 is bound with solid-phase carrier 82*a*, it is possible to easily separate immune complex 85 and the other components through BF separation.

In the configuration example illustrated in FIG. 2, after the first solid phasing processing, controller 104 controls the first test processing further including first BF separation processing of discarding a liquid phase separated in the BF separation by BF separation part 30, and second BF separation processing of dispensing immune complex 85 released from first solid-phase carrier 82*a* by releasing reagent 86 into second reaction container 71. Consequently, it is possible to easily separate, with the first BF separation processing, immune complex 85 bound with first solid-phase carrier 82*a* from the other components. It is possible to separate, with the second BF separation processing, immune complex 85 released from first solid-phase carrier 82*a* from first solid-phase carrier 82*a*.

In the configuration example illustrated in FIG. 2, controller 104 controls the first test processing so as to perform the second BF separation processing between the releasing processing and the second solid phasing processing. Consequently, it is possible to easily separate, with the second BF separation processing, immune complex 85 before being released from first solid-phase carrier 82*a* and bound with second solid-phase carrier 82*b*.

In the configuration example illustrated in FIG. 2, controller 104 controls the first test processing such that first reaction container discarding processing of discarding first reaction container 70 is performed between the second BF separation processing and the second solid phasing processing. Consequently, since the used first reaction container 70 is discarded, it is unnecessary to transfer used first reaction container 70 with the transfer unit 50.

In the configuration example illustrated in FIG. 2, controller 104 controls the first test processing such that third BF separation processing of discarding a liquid phase separated by BF separation processing 30 is performed between the second solid phasing processing and the measurement processing. Consequently, it is possible to easily separate, with the third BF separation processing, immune complex 85 bound with second solid-phase carrier 82b from the other components.

In the configuration example illustrated in FIG. 2, controller 104 controls second test processing. The second test processing includes the third solid phasing processing of binding target substance 81, labeled substance 83, and third solid-phase part 82c, and the second test processing includes the measurement processing of measuring a signal. That is, controller 104 controls the second test processing of performing the immunoassay for not carrying out the immune complex transfer method. Consequently, it is possible to perform, with one immunoassay apparatus 100, both of the immune chemical measurement in which the immune complex transfer method is not used and high-sensitivity immune performance in which the immune complex transfer method is used.

In the configuration example illustrated in FIG. 2, controller 104 allocates first reaction container 70 to the second test processing for the measurement order. Consequently, it is possible to surely prepare one first reaction container 70 for the immune chemical measurement for not carrying out the immune complex transfer method.

In the configuration example illustrated in FIG. 2, in a case where measurement orders coexist for the first test processing and the second test processing, controller 104 perform control such that the first test processing for a first measurement order and the second test processing for a second measurement order are concurrently performed by allocating first reaction container 70 and second reaction container 71 to the first test processing and allocating first reaction container 70 to the second test processing. Consequently, even when the measurement order for the first test processing and the measurement order for the second test processing coexist, it is possible to surely prepare reaction containers for both of the first test processing and the second test processing. In this case, controller 104 may perform control such that processing timings of the first test processing and the second test processing to at least partly overlap each other. Consequently, it is possible to prevent a time of the test processing from increasing.

Measurement mechanism part 102 includes a sample dispensing arm 12 as sample dispenser part 10. Sample dispensing arm 12 is movable. After first dispensing tip 11a is attached to sample dispensing arm 12 in tip attachment position 220, sample dispensing arm 12 aspirates a sample in a test tube conveyed to a sample aspiration position 210 by sample conveyance part 103 and dispenses the sample into first reaction container 70 of reaction-container holding part 60. Consequently, immune complex 85 for the immune complex transfer method can be dispensed by sample dispenser part 10 for dispensing the sample. After second dispensing tip 11b is attached to sample dispensing arm 12 in tip attachment position 220, sample dispensing arm 12 aspirates the supernatant liquid including immune complex 85 from first reaction container 70 of reaction-container holding part 60 and dispenses immune complex 85 into second reaction container 71 of reaction-container holding part 60.

Dispensing tip 11 is retained in dispensing-tip supply part 111. Dispensing-tip supply part 111 is capable of receiving a large number of dispensing tips 11 and conveying received dispensing tips 11 to tip attachment position 220 one by one. Dispensing tips 11 of the same type are used as first dispensing tip 11a and second dispensing tip 11b. To sample dispensing arm 12, first dispensing tip 11a and second dispensing tip 11b are attached at common tip attachment position 220. Consequently, the apparatus configuration can be simplified compared with a case where two or more dispensing-tip supply parts 111 are provided and the attachment of first dispensing tip 11a and the attachment of second dispensing tip 11b are performed at separate positions. Meanwhile, in a case where dispensing tips of different types are used as first dispensing tip 11a and second dispensing tip 11b, for example, two or more dispensing-tip supply parts 111 may be provided.

When sample dispenser part 10 performs dispensing via dispensing tip 11, sample dispenser part 10 aspirates immune complex 85 from first reaction container 70 via second dispensing tip 11b attached by replacing first dispensing tip 11a and dispenses immune complex 85 into second reaction container 71. Since first dispensing tip 11a is replaced with second dispensing tip 11b, carryover of the sample via dispensing tip 11 is prevented. In a case where the dispensing of immune complex 85 by sample dispenser part 10 is carried out by replacing first dispensing tip 11a, which is used when the sample is dispensed, with second dispensing tip 11b, contamination of the sample is prevented.

Containers of the same type are used as first reaction container 70 and second reaction container 71. First reaction container 70 and second reaction container 71 are retained in container supply part 112. Container supply part 112 is capable of receiving a large number of containers and sequentially supplying first reaction containers 70 or second reaction containers 71 to reaction-container holding part 60 one by one.

Reaction-container holding part 60 includes holding holes 61 for holding first reaction container 70 and second reaction container 71. The configuration of reaction-container holding part 60 is explained below.

Measurement mechanism part 102 includes, as reagent dispenser part 20, first reagent dispenser unit 21, second reagent dispenser unit 22, third reagent dispenser unit 23, and fourth reagent dispenser unit 24.

First reagent dispenser unit 21, second reagent dispenser unit 22, and third reagent dispenser unit 23 each include one pipette 25. First reagent dispenser unit 21, second reagent dispenser unit 22, and third reagent dispenser unit 23 can move pipettes 25 of the units to a predetermined reagent aspiration position and a reagent dispensing position.

First reagent dispenser unit 21 aspirates, with pipette 25, an R1 reagent from a reagent container set in reagent setting part 113 and dispenses the aspirated R1 reagent to first reaction container 70 placed on reaction-container holding part 60. First reagent dispenser unit 21 aspirates, with pipette 25, an r1 reagent from the reagent container set in reagent setting part 113 and dispenses the aspirated r1 reagent into first reaction container 70 placed on reaction-container holding part 60.

Second reagent dispenser unit 22 can aspirate, with pipette 25, an R3 reagent and an R5 reagent from the respective reagent containers set in reagent setting part 113 and dispense the aspirated R3 and R5 reagents into first reaction container 70, respectively. Second reagent dispenser unit 22 can aspirate an R7 reagent from the reagent container set in reagent setting part 113 and dispense the aspirated R7 reagent into second reagent container 71. Second reagent dispenser unit 22 dispenses a reagent into first reaction container 70 or second reaction container 71 conveyed to reagent dispensing position 230. Note that, as explained below, the R5 reagent and the R7 reagent respectively contain first solid-phase carrier 82a and second solid-phase carrier 82b (see FIG. 6). In this way, reagent dispenser part 20 is configured to dispense a first solid-phase reagent (the R5 reagent) into first reaction container 70 and to dispense a second solid-phase reagent (the R7 reagent) into second reaction container 71 which stores immune complex 85 dispensed. Second reagent dispenser unit 22 aspirates, with pipette 25, an r2 reagent from the reagent container set in reagent setting part 113 and dispenses the aspirated r2 reagent into first reaction container 70 transferred to reagent dispensing position 230. Note that, as explained below, the r2 reagent contains third solid-phase carrier 82c (see FIG. 8). In this way, reagent dispenser part 20 is configured to dispense the third solid-phase reagent (the r2 reagent) into first reaction container 70.

Third reagent dispenser unit 23 can aspirate, with pipette 25, an R2 reagent and a R4 reagent from the respective reagent containers set in reagent setting part 113 and dispense the aspirated R2 and R4 reagents into first reaction container 70, respectively. The third regent dispenser unit 23 dispenses the reagent into first reaction container 70 conveyed to reagent dispensing position 240. Third reagent dispenser unit 23 aspirates, with pipette 25, an r3 reagent from the reagent container set in reagent setting part 113 and dispenses the aspirated r3 reagent into first reaction container 70 transferred to reagent dispensing position 240.

Fourth reagent dispenser unit 24 includes dispenser part 24a that dispenses the R8 reagent into second reaction container 71 and dispenser part 24b that dispenses the R9 reagent into second reaction container 71. Dispenser part 24a and dispenser part 24b are respectively connected to not-illustrated reagent containers that store the R8 reagent and the R9 reagent. Dispenser part 24a and dispenser part 24b respectively dispense the reagent into second reaction container 71 transferred to the positions of dispenser part 24a and dispenser part 24b. Dispenser part 24a dispenses the r4 reagent (the R8 reagent) into first reaction container 70 transferred to the position of dispenser part 24a. Dispenser part 24b dispenses the r5 reagent (the R9 reagent) into first reaction container 70 transferred to the position of dispenser part 24b.

Figure 3:
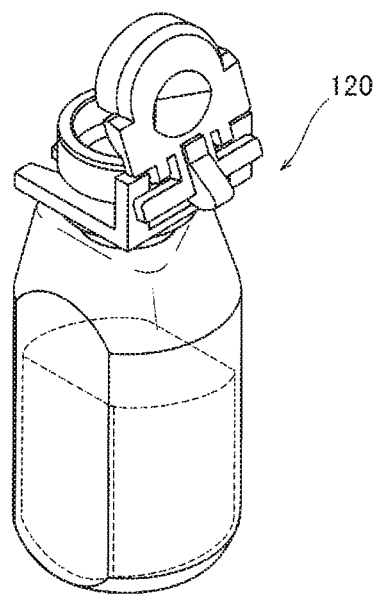
FIG. 3 is a perspective view illustrating an example of a reagent container.

Reagent setting part 113 is configured to be capable of housing reagent containers 120 that store reagents. Reagent containers 120 have, for example, a bottle shape illustrated in FIG. 3. Reagent containers 120 store the reagent in the inside. Reagent containers 120 are provided for respective types of reagents and are individually set in reagent setting part 113. That is, in this embodiment, according to a reagent to be stored, seven types of reagent containers 120 for the R1 reagent and the R7 reagent are set in reagent setting part 113. Note that the reagent container (not illustrated) for the R8 reagent connected to dispenser part 24a and the reagent container (not illustrated) for the R9 reagent connected to dispenser part 24b are set in a setting part (not illustrated) different from reagent setting part 113.

Referring back to FIG. 2, first reagent dispenser unit 21 to third reagent dispenser unit 23 can aspirate the reagent via respective pipettes 25 though aspiration windows (not illustrated) provided in respective reagent aspiration positions of reagent setting part 113.

Measurement mechanism part 102 includes first separation part 30a and second separation part 30b as BF separation part 30. First separation part 30a performs the first BF separation processing for immune complex 85 in first reaction container 70 which stores the first solid-phase reagent (the R5 reagent) dispensed. Second separation part 30b performs the third BF separation processing for immune complex 85 in second reaction container 71 which stores the second solid-phase reagent (the R7 reagent) dispensed. The first BF separation processing is separation processing of separating first solid-phase carrier 82a (see FIG. 6), on which immune complex 85 including target substance 81 and labeled substance 83 is formed, and a liquid component. The third BF separation processing is separation processing of separating second solid-phase carrier 82b (see FIG. 6), on which immune complex 85 including target substance 81 and labeled substance 83 is formed, and releasing reagent 86. The configuration may be common to first separation part 30a and second separation part 30b. Details are explained below. The first separation part 30a performs primary BF separation processing for third solid-phase carrier 82c (see FIG. 8) in first reaction container 70 which stores the third solid-phase reagent (the r2 reagent) dispensed. The second separation part 30b performs secondary BF separation processing for immune complex 85 in first reaction container 70 which stores the third solid-phase reagent (the r2 reagent) dispensed.

Measurement mechanism part 102 includes measurement part 40 including a photomultiplier tube. Measurement part 40 acquires, with the photomultiplier tube, light generated in a reaction process between labeled substance 83 bound to target substance 81 and a light emitting substrate to thereby measure an amount of an antigen included in the sample.

Measurement mechanism part 102 includes transfer units as transfer part 50. Transfer part 50 includes container holding part 51 and reaction-container transfer part 52.

Container holding part 51 includes holding holes 51a for holding first reaction container 70 and second reaction container 71 and provides setting positions of first reaction container 70 and second reaction container 71. Container holding part 51 is capable of sequentially transferring first reaction container 70 and second reaction container 71 held by holding holes 51a. In the configuration example illustrated in FIG. 2, container holding part 51 is formed in an annular shape along the outer circumference of circular reagent setting part 113 and can rotate and turn in the circumferential direction. In container holding part 51, a large number of holding holes 51a are formed along the circumferential direction of holding holes 51a. Container holding part 51 can collectively move first reaction container 70 and second reaction container 71 held by holding holes 51a in the circumferential direction. In this embodiment, container holding part 51 rotates and moves in an A1 direction.

Container 51 may have a function of warming or maintaining first reaction container 70 and second reaction container 71 held by holding holes 51a to a predetermined temperature. In the configuration example illustrated in FIG. 2, container holding part 51 performs transfer of the container in the A1 direction while performing temperature adjustment of first reaction container 70 and second reaction container 71 held in the holding holes 51a.

Reaction-container transfer part 52 has a function to transfer first reaction container 70 and second reaction container 71 between container holding part 51 and the parts such as sample dispenser part 10, reagent dispenser part 20, BF separation part 30, and measurement part 40. Reaction-container transfer part 52 is a catcher unit that can pick and move first reaction containers 70 and second reaction containers 71 one by one. Reaction-container transfer parts 52 are provided in measurement mechanism part 102.

Reaction-container transfer part 52a can transfer first reaction container 70 and second reaction container 71 between reaction-container holding part 60 and container holding part 51. Reaction-container transfer part 52a can transfer first reaction container 70 or second reaction container 71 held by reaction-container holding part 60 to holding hole 51a positioned in first position 250 of container holding part 51. Reaction-container transfer part 52a can transfer first reaction container 70 held in holding hole 51a positioned in fourth position 280 of container holding part 51 to transfer holding hole 61 of reaction-container holding part 60. First position 250 and fourth position 280 may be the same position or may be different positions. In FIG. 2, an example is illustrated in which first position 250 and the fourth position 280 are present in the same position. That is, a position (first position 250) where reaction-container transfer part 52a sets first reaction container 70 or second reaction container 71 and a position (fourth position 280) where reaction-container transfer part 52a takes first reaction container 70 from container holding part 51 are the same position. In a case where target first reaction container 70 is positioned in fourth position 280 by container holding part 51, reaction-container transfer part 52a takes target first reaction container 70. Reaction-container transfer part 52a sets first reaction container 70 or second reaction container 71 in holding hole 51a located in first position 250 when set timing of first reaction container 70 comes.

Reaction-container transfer part 52b can transfer first reaction container 70 between container holding part 51 and first separation part 30a. Reaction-container transfer part 52b can transfer first reaction container 70, which is held by holding hole 51a positioned in second position 260 of container holding part 51, to first separation part 30a. Reaction-container transfer part 52b can transfer first reaction container 70 from first separation part 30a to holding hole 51a positioned in third position 270 of container holding part 51.

Reaction-container transfer part 52c can transfer first reaction container 70 and second reaction container 71 between container holding part 51 and second separation part 30b. Reaction-container transfer part 52b can transfer first reaction container 70 or second reaction container 71, which is held by holding hole 51a positioned in fifth position 290 of container holding part 51, to second separation part 30b. Reaction-container transfer part 52b can transfer first reaction container 70 or second reaction container 71 from second separation part 30b to sixth position 300.

Reaction-container transfer part 52d can transfer second reaction container 71 and first reaction container 70 among sixth position 300, container holding part 51, and fourth reagent dispenser unit 24. Reaction-container transfer part 52e can transfer second reaction container 71 and first reaction container 70 between container holding part 51 and measurement part 40. Reaction-container transfer part 52e transfers, to discarding port 114, second reaction container 71 and first reaction container 70 after the measurement, and first reaction container 70 after the aspiration of the supernatant liquid, and discards second reaction container 71 and first reaction containers 70.

By providing container holding part 51 and reaction-container transfer part 52 as transfer part 50 in this way, reaction-container transfer part 52 can individually transfer first reaction containers 70 to reaction-container holding part 60 and BF separation part 30 while container holding part 51 holds and collectively transfers first reaction containers 70 and second reaction containers 71. As a result, it is possible to simplify the configuration of transfer part 50 compared with a case where individual first reaction containers 70 and second reaction containers 71 are, without being collectively transferred, completely transferred one by one.

Configuration Example of the BF Separation Part

Figure 4:
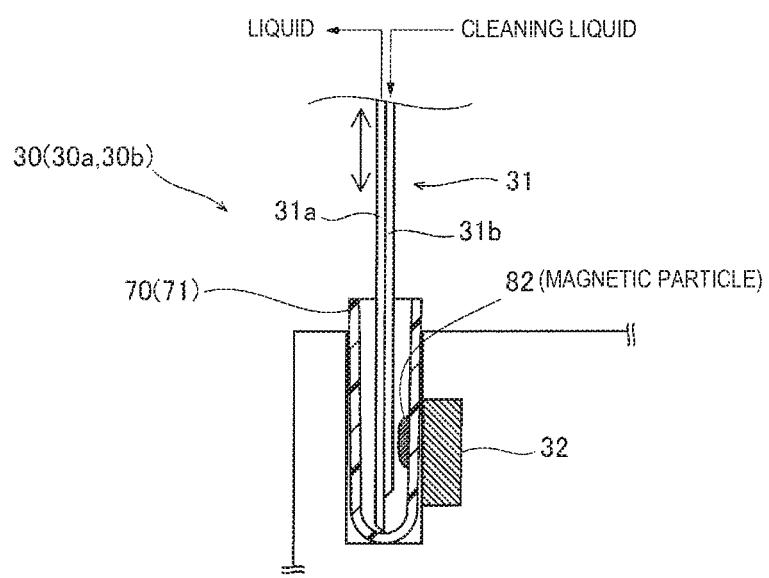
FIG. 4 is a schematic diagram illustrating a BF separation part of an immunoassay apparatus according to an embodiment.

Since first separation part 30a and second separation part 30b have a common configuration, first separation part 30a and second separation part 30b are collectively explained as BF separation part 30. BF separation part 30 includes cleaning part 31, for example, as illustrated in FIG. 4. Cleaning part 31 includes aspiration tube 31a for aspirating liquid including unreacted labeled substance 83 and discharge tube 31b for discharging cleaning liquid into first reaction container 70 or second reaction container 71.

In a case where the magnetic particle is used as solid-phase carrier 82, BF separation part 30 may include first magnetism collection part 32 for collecting solid-phase carrier 82 (the magnetic particle) on which immune complex 85 including target substance 81 and labeled substance 83 is formed. First magnetism collection part 32 is capable of generating a magnetic force caused to act on the magnetic particle and is, for example, a permanent magnet or an electronic magnet. BF separation part 30 is capable of holding first reaction container 70 or second reaction container 71. First magnetism collection part 32 is set near first reaction container 70 or second reaction container 71 held by BF separation part 30. In FIG. 4, a configuration example is illustrated in which first magnetism collection part 32 is disposed in a position adjacent to a side surface of first reaction container 70 set in BF separation part 30 and solid-phase carrier 82 (the magnetic particle) is collected to the inner side surface of first reaction container 70.

In this case, in a state in which the magnetic particle is collected by first magnetism collection part 32, cleaning part 31 aspirates and removes a liquid component including unreacted labeled substance 83 and cleans the magnetic particle with the cleaning liquid. Consequently, an unnecessary component is removed, by the BF separation processing, from a specimen including immune complex 85 bound with solid-phase carrier 82.

Configuration Example of Reaction-Container Holding Part

Figure 5:
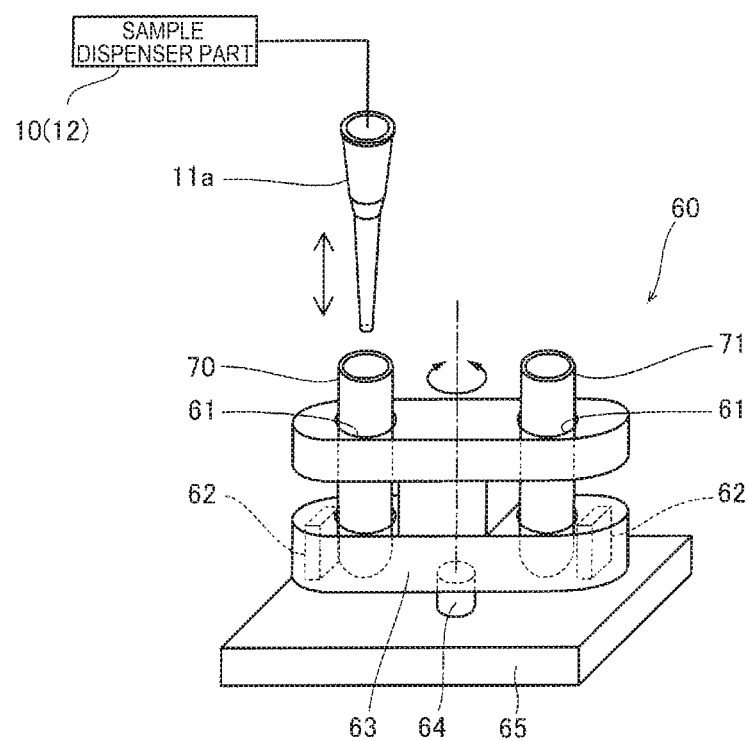
FIG. 5 is a schematic perspective view illustrating a reaction-container holding part of an immunoassay apparatus according to an embodiment.

For example, as illustrated in FIG. 5, reaction-container holding part 60 includes holding holes 61.

Reaction-container holding part 60 is capable of setting first reaction container 70 in one of holding holes 61 and setting second reaction container 71 in another one holding hole 61. That is, reaction-container holding part 60 can hold first reaction container 70 and second reaction container 71 in respective holding holes 61. In FIG. 5, two holding holes 61 are provided.

In this case, sample dispenser part 10 dispenses immune complex 85 in first reaction container 70 held by reaction-container holding part 60 into second reaction container 71 held by reaction-container holding part 60. Consequently, it is possible to quickly perform an aspiration operation and a dispensing operation of immune complex 85 compared with a case, for example, where aspirated first reaction container 70 is replaced with new second reaction container 71 in reaction-container holding part 60 and then immune complex 85 is dispensed into second reaction container 71.

In a case where the magnetic particle is used as solid-phase carrier 82, immunoassay apparatus 100 may include second magnetism collecting part 62 for collecting the magnetic particle in first reaction container 70 held by holding hole 61 of reaction-container holding part 60. In this case, in a state in which the magnetic particle is collected by second magnetism collection part 62, sample dispenser part 10 aspirates, via second dispensing tip 11b, released immune complex 85 in first reaction container 70. Consequently, it is possible to quickly and effectively separate immune complex 85 and solid-phase carrier 82 (the magnetic particle) with a magnetic force of second magnetism collection part 62. As a result, it is possible to effectively suppress carryover of solid-phase carrier 82 when immune complex 85 is dispensed into second reaction container 71.

Second magnetism collection part 62 is capable of generating a magnetic force caused to act on the magnetic particle and is, for example, a permanent magnet or an electric magnet. Second magnetism collection part 62 is disposed, for example, near the bottom of holding hole 61. Sample dispenser part 10 aspirates the supernatant liquid in first reaction container 70 to thereby aspirate released immune complex 85. Consequently, it is possible to collect solid-phase carrier 82 in a position kept away from an aspiration position of immune complex 85 (i.e., an upper part of first reaction container 70) as much as possible.

Second magnetism collection part 62 may be disposed to be adjacent to the outside of reaction-container holding part 60 or may be attached to holding member 63 of reaction-container holding part 60 as illustrated in FIG. 5. In FIG. 5, an example is illustrated in which second magnetism collection parts 62 are set in respective two holding holes 61. However, second magnetism collection part 62 may be provided in only one holding hole 61. In that case, reaction-container transfer part 52a transfers first reaction container 70 to holding hole 61 in which second magnetism collection part 62 is provided and transfers second reaction container 71 to holding hole 61 in which second magnetism collection part 62 is not provided. In a case where second magnetism collection parts 62 are set in respective holding holes 61, it is possible to set first reaction container 70 and second reaction container 71 in any holding holes 61.

Reaction-container holding part 60 may be movable such that the positions of holding holes 61 can be replaced with one another. For example, reaction-container holding part 60 includes driving part 65 that rotates holding member 63, in which holding holes 61 are provided, around rotating shaft 64. In this case, holding holes 61 are disposed in positions at equal distances in the radial direction centering on rotating shaft 64 and are capable of exchanging their positions with one another. Consequently, it is possible to fix a dispensing position of sample dispenser part 10 and sequentially dispose, according to the rotation of holding member 63, in the dispensing position, first reaction container 70 and second reaction container 71 set in holding holes 61. It is possible to quickly perform the aspiration operation and the dispensing operation of immune complex 85 compared with a case where the aspiration and the dispensing of immune complex 85 in different positions.

(Overview of the Immunoassay by the First Test Processing)

Figure 6:
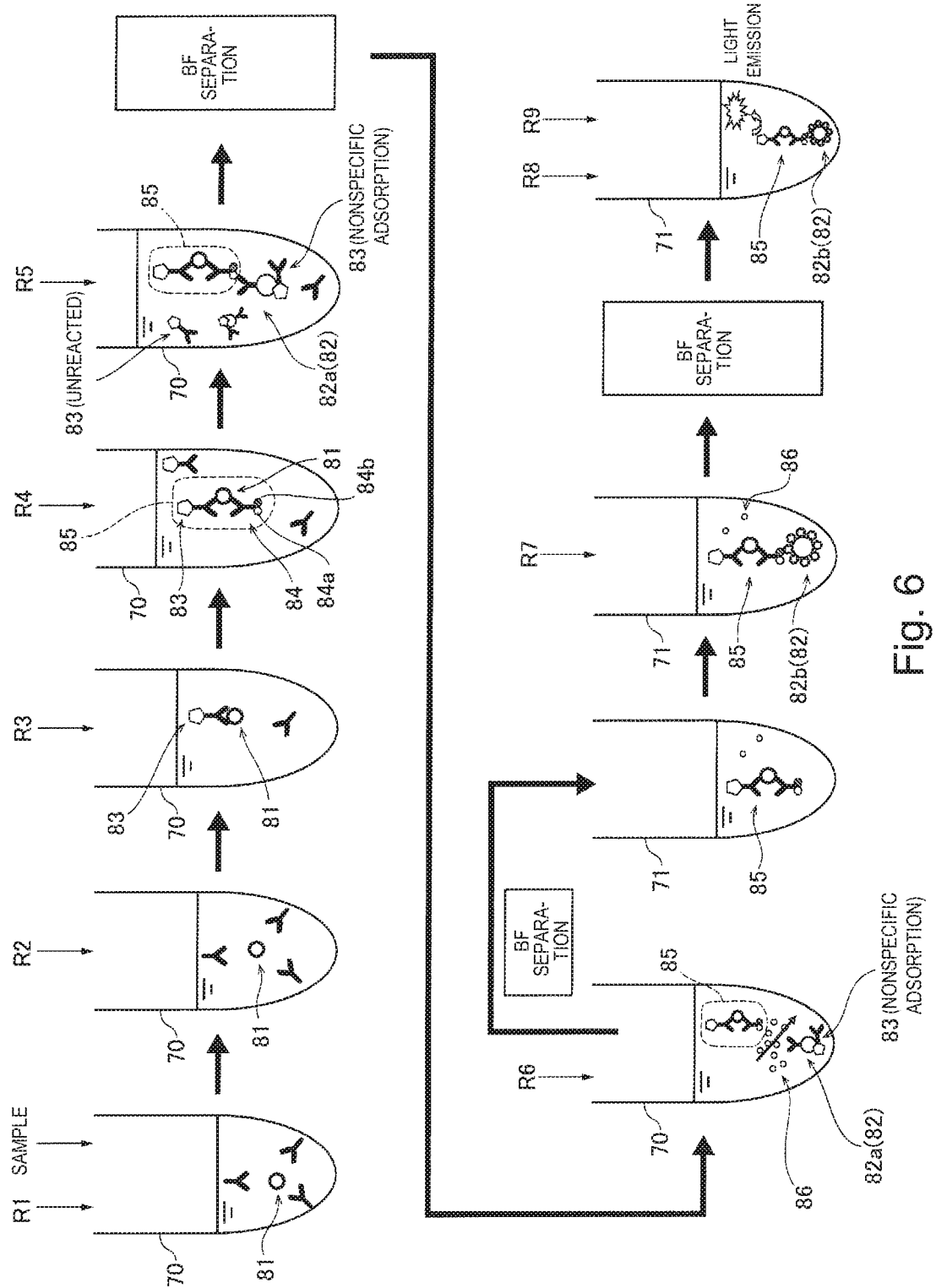
FIG. 6 is a diagram illustrating an overview of immunoassay by first test processing of an immunoassay apparatus illustrated in FIG. 2.

In the configuration example illustrated in FIG. 2, as illustrated in FIG. 6, the immunoassay is performed using the R1 reagent to the R9 reagent. In an example illustrated in FIG. 6, the first test processing of performing high-sensitivity immunoassay in which the immune complex transfer method is used is explained. As an example of the immunoassay, an example is explained in which target substance 81 is a hepatitis B surface antigen (HBsAg).

First, a sample including target substance 81 and the R1 reagent are dispensed into first reaction container 70. The R1 reagent is a reagent that contains an alkaline substance and denatures the sample with alkali. The R1 reagent releases, from an antibody, an antigen present in the sample in a state in which the antibody is bound with the antigen in advance. Subsequently, the R2 reagent is dispensed into first reaction container 70. The R2 reagent a neutralization reagent that includes an acid substance and neutralizes alkali of the sample after the R1 reagent dispensing. The R1 reagent and the R2 reagent are dispensed as pretreatment for releasing, from the antibody, the antigen present in the sample in a state in which the antibody is bound with the antigen in advance. Depending on target substance 81, it is unnecessary to dispense the R1 reagent and the R2 reagent.

Subsequently, the R3 reagent is dispensed into first reaction container 70. The R3 reagent contains labeled substance 83 and reacts with target substance 81 to be bound with target substance 81. Consequently, labeled substance binding processing is performed. In the example illustrated in FIG. 6, labeled substance 83 is an ALP (alkaline phosphatase) labeled antibody.

Subsequently, the R4 reagent is dispensed into first reaction container 70. The R4 reagent contains capturing substance 84 and reacts with target substance 81 to be bound with target substance 81. Capturing substance 84 includes first binding substance 84a for capturing substance 84 to be bound with first solid-phase carrier 82a and second binding substance 84b for capturing substance 84 to be bound with second solid-phase carrier 82b. First binding substance 84a and second binding substance 84b are substances bound with a solid-phase carrier by binding abilities different from each other.

For the binding of the binding substance and the solid-phase carrier, for example, combinations, such as biotin and avidins, hapten and an anti-hapten antibody, nickel and a histidine tag, and glutathione and glutathione-S-transferase can be used. Note that the "avidins" means that the avidins include avidin and streptavidin.

In this embodiment, capturing substance 84 is an antibody (a DNP/biotin antibody) modified by DNP (dinitrophenyl group) and biotin. That is, in capturing substance 84, DNP (dinitrophenyl group) is modified as first binding substance 84a and biotin is modified as second binding substance 84b.

Subsequently, the R5 reagent is dispensed into first reaction container 70. The R5 reagent contains first solid-phase carrier 82a as solid-phase carrier 82. First solid-phase carrier 82a is a magnetic particle to which the anti-DNP antibody is fixed (an anti-DNP antibody-converted magnetic particle). The anti-DNP antibody of the anti-DNP antibody-converted magnetic particle reacts with the DNP of capturing substance 84, which is hapten, to be bound with the DNP. As a result, immune complex 85 including target substance 81, labeled substance 83, and capturing substance 84 is formed on first solid-phase carrier 82a. Consequently, first solid-phase carrier binding processing is performed. The first solid-phase carrier binding processing is performed after the labeled substance binding processing, whereby the first solid phasing processing is performed.

Immune complex 85 formed on first solid-phase carrier 82*a* and unreacted labeled substance 83 are separated by first BF separation processing. Unnecessary components such as unreacted labeled substance 83 are removed from first reaction container 70.

Subsequently to the first BF separation processing, the R6 reagent is dispensed into first reaction container 70. The R6 reagent is releasing reagent 86. Releasing reagent 86 cancels the biding of first binding substance 84*a* of capturing substance 84 and first solid-phase carrier 82*a*. Consequently, releasing processing is performed. Releasing reagent 86 is selected according to a type of the binding of first binding substance 84*a* and first solid-phase carrier 82*a*.

For example, in a case where the binding of first binding substance 84*a* and first solid-phase carrier 82*a* is binding by hapten-anti-hapten antibody, hapten or a hapten derivative can be used as releasing reagent 86. In a case where the binding of first binding substance 84*a* and first solid-phase carrier 82*a* is binding by ion binding, a solution including ion can be used as releasing reagent 86. In a case where the binding of first binding substance 84*a* and first solid-phase carrier 82*a* is binding by ligand-receptor functioning as separable binding, ligand or a ligand analogue can be used as releasing reagent 86. In a case where the binding of first binding substance 84*a* and first solid-phase carrier 82*a* is binding by lectin-sugar chain functioning as separable binding, sugar can be used as releasing reagent 86. In a case where the binding of first binding substance 84*a* and first solid-phase carrier 82*a* is binding by biotin-avidin, biotin can be used as releasing reagent 86.

In the example illustrated in FIG. 6, DNP-Lys (DNP-Lysine) is used as releasing reagent 86. The DNP-Lys reacts with the anti-DNP antibody-converted magnetic particle, which is first solid-phase carrier 82*a*, to be bound with the anti-DNP antibody-converted magnetic particle. Therefore, when the R6 reagent is dispensed into first reaction container 70, binding of the DNP of capturing substance 84 and first solid-phase carrier 82*a* and binding of releasing reagent 86 (DNP-Lys) and first solid-phase carrier 82*a* conflict, and immune complex 85 is dissociated from first solid-phase carrier 82*a*.

Immune complex 85 released by the R6 reagent is aspirated from first reaction container 70 by sample dispenser part 10 and dispensed into another container (second reaction container 71). Consequently, the supernatant liquid including immune complex 85 released from first solid-phase carrier 82*a* is transferred from first reaction container 70 to second reaction container 71. First solid-phase carrier 82*a* remains in first reaction container 70 after the supernatant liquid including immune complex 85 is aspirated. As a result, labeled substance 83 nonspecifically bound with first solid-phase carrier 82*a* is separated from immune complex 85. Consequently, the second BF separation processing is performed.

Subsequently, the R7 reagent is dispensed into second reaction container 71 which stores immune complex 85 dispensed. The R7 reagent contains second solid-phase carrier 82*b* as solid-phase carrier 82. Solid-phase carrier 82*b* is bound with second binding substance 84*b* of capturing substance 84. Second solid-phase carrier 82*b* is a magnetic particle to which streptavidin that can bind with biotin is fixed (a StAvi-bound magnetic particle). The streptavidin of the StAvi-bound magnetic particle reacts with biotin, which is second binding substance 84*b*, to be bound with the biotin. As a result, immune complex 85 including target substance 81, labeled substance 83, and capturing substance 84 is bound with second solid-phase carrier 82*b*. Consequently, the second solid phasing processing is performed.

Immune complex 85 bound with second solid-phase carrier 82*b* and an unnecessary component other than second solid-phase carrier 82*b*, on which immune complex 85 is formed, are separated by the third BF separation processing, and the unnecessary component is removed from second reaction container 71. The unnecessary component is, for example, releasing reagent 86 included in the supernatant liquid, labeled substance 83 included in the supernatant liquid together with immune complex 85 without being bound with target substance 81, and the like. In this way, performed are both of separation processing (the first BF separation processing) for immune complex 85 in first reaction container 70 which stores the dispensed solid-phase reagent (the R5 reagent) including first solid-phase carrier 82*a*, and separation processing for immune complex 85 in second reaction container 71 which stores the dispensed solid-phase reagent (the R7 reagent) including second solid-phase carrier 82*b*. Consequently, an unnecessary component mixed together with immune complex 85 when immune complex 85 is transferred from first reaction container 70 to second reaction container 71 can be removed. Therefore, it is possible to further reduce a background signal in the immunoassay.

Thereafter, the R8 reagent and the R9 reagent are dispensed into second reaction container 71. The R8 reagent contains a buffer solution. Immune complex 85 bound with second solid-phase carrier 82*b* is dispersed in the buffer solution. The R9 reagent contains a chemical light emitting substrate. The buffer solution contained in the R8 reagent has a composition for facilitating a reaction between a label (an enzyme) of labeled substance 83 included in immune complex 85 and the substrate. Light is generated by causing the substrate to react with the label. The intensity of the generated light is measured by measurement part 40.

(Explanation of an Immune Measurement Processing Operation by the First Test Processing)

Figure 7:
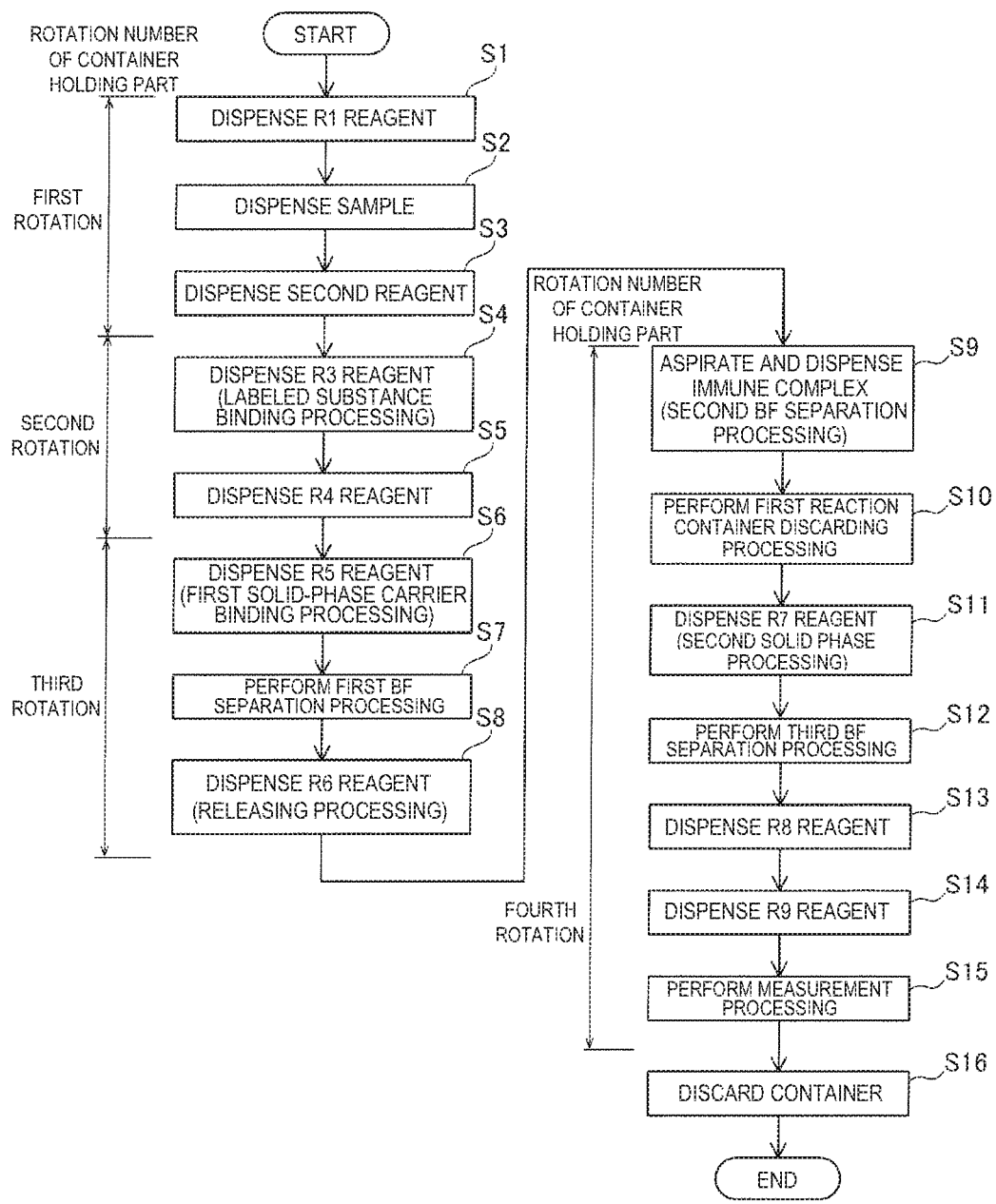
FIG. 7 is a flowchart illustrating a measurement processing operation by first test processing of an immunoassay apparatus according to an embodiment.

A measurement processing operation of immunoassay apparatus 100 illustrated in FIG. 2 is explained with reference to FIG. 7. In an example illustrated in FIG. 7, the first test processing of performing the high-sensitivity immunoassay in which the immune complex transfer method is used is explained. In the following explanation, FIG. 7 is referred to concerning steps of the measurement processing operation and FIG. 2 is referred to concerning the parts of immunoassay apparatus 100.

In the measurement, container holding part 51 rotates by a unit pitch clockwise (in an A1 direction) at every predetermined time interval. Reaction-container transfer part 52 performs container transfer between container holding part 51 and sample dispenser part 10, reagent dispenser part 20, and BF separation part 30 according to timings of the processes in sample dispenser part 10, reagent dispenser part 20, and BF separation part 30. When focusing on measurement of one sample, in this embodiment, container holding part 51 makes four rotations from the dispensing of the sample until the sample is transferred to measurement part 40.

Processes in steps S1 to S3 are executed in first rotation of container holding part 51. In step S1, the R1 reagent is dispensed into first reaction container 70. First, first reaction container 70 is supplied from container supply part 112 to reaction-container holding part 60. First reagent dispenser unit 21 dispenses the R1 reagent into first reaction container 70 held by reaction-container holding part 60.

In step S2, a sample is dispensed into first reaction container 70. First dispensing tip 11a is attached to sample dispenser part 10 in tip attachment position 220. Sample dispenser part 10 aspirates the sample in sample aspiration position 210. Sample dispenser part 10 dispenses the aspirated sample into first reaction container 70 held by reaction-container holding part 60. After the dispensing, first dispensing tip 11a is discarded to a not-illustrated discarding port. Sample dispenser part 10 repeats twice a sample dispensing operation including, as a unit sequence, the attachment of first dispensing tip 11a, the aspiration of the sample, the dispensing of the sample, and the discarding of first dispensing tip 11a. Consequently, the sample of a double amount of a unit amount dispensable by dispensing tip 11 is dispensed into first reaction container 70. Every time sample dispenser part 10 performs a dispensing operation via first dispensing tip 11a, sample dispenser part 10 replaces first dispensing tip 11a with unused dispensing tip 11 (unused first dispensing tip 11a).

After the dispensing of the sample, reaction-container transfer part 52a transfers first reaction container 70 to holding hole 51a positioned in the first position 250 of container holding part 51.

When first reaction container 70 is transferred to reagent dispensing position 240 of third reagent dispenser unit 23 by container holding part 51, in step S3, the R2 reagent is dispensed into first reaction container 70. Third reagent dispenser unit 23 dispenses the R2 reagent into first reaction container 70 held by container holding part 51. The processing performed in the first rotation of container holding part 51 in steps S1 to S3 is completed.

In the second rotation of container holding part 51, processes in steps S4 and S5 are executed. In step S4, the R3 reagent is dispensed into first reaction container 70. When first reaction container 70 is transferred to reagent dispensing position 230 of second reagent dispenser unit 22 by container holding part 51, second reagent dispenser unit 22 dispenses the R3 reagent into first reaction container 70 held by container holding part 51. Consequently, labeled substance binding processing is performed.

In step S5, the R4 reagent is dispensed into first reaction container 70. When first reaction container 70 is transferred to reagent dispensing position 240 of third reagent dispenser unit 23 by container holding part 51, third reagent dispenser unit 23 dispenses the R4 reagent into first reaction container 70 held by container holding part 51. The processing performed in the second rotation of container holding part 51 in steps S4 and S5 is completed.

In the third rotation of container holding part 51, processes in steps S6 to S8 are executed. In step S6, the R5 reagent is dispensed into first reaction container 70. When first reaction container 70 is transferred to reagent dispensing position 230 of second reagent dispenser unit 22 by container holding part 51, second reagent dispenser unit 22 dispenses the R5 reagent into first reaction container 70 held by container holding part 51. Consequently, first solid-phase carrier binding processing is performed.

In step S7, the first BF separation processing is performed by first separation part 30a. First, when first reaction container 70 is transferred to second position 260 by container holding part 51, reaction-container transfer part 52b takes first reaction container 70 and transfers first reaction container 70 to first separation part 30a.

First separation part 30a performs the first BF separation processing on a specimen in first reaction container 70 and removes a liquid component. When the first BF separation processing ends, reaction-container transfer part 52b sets first reaction container 70 in holding hole 51a positioned in third position 270 of container holding part 51.

In step S8, the R6 reagent is dispensed into first reaction container 70. When first reaction container 70 is transferred to reagent dispensing position 240 of third reagent dispenser unit 23 by container holding part 51, third reagent dispenser unit 23 dispenses the R6 reagent into first reaction container 70 held by container holding part 51. Consequently, releasing processing is performed. The processing performed in the third rotation of container holding part 51 in steps S6 to S8 is completed.

In the fourth rotation of container holding part 51, processes in steps S9 to S15 are executed. In step S9, immune complex 85 is aspirated from first reaction container 70. When first reaction container 70 is transferred to fourth position 280 by container holding part 51, reaction-container transfer part 52a takes first reaction container 70 and transfers first reaction container 70 to holding hole 61 of reaction-container holding part 60. A new container is supplied from container supply part 112 to reaction-container holding part 60 as second reaction container 71. First reaction container 70 and second reaction container 71 are set in respective holding holes 61 of reaction-container holding part 60. A magnetic particle in first reaction container 70 is collected to the bottom of first reaction container 70 by second magnetism collection part 62.

Subsequently, second dispensing tip 11b is attached to sample dispenser part 10 in tip attachment position 220. Sample dispenser part 10 aspirates immune complex 85 by aspirating the supernatant liquid from first reaction container 70 held by reaction-container holding part 60. Thereafter, reaction-container holding part 60 replaces the position of first reaction container 70 after aspiration and the position of second reaction container 71. Sample dispenser part 10 dispenses immune complex 85 into second reaction container 71 held by reaction-container holding part 60. Consequently, the second BF separation processing is performed. After the dispensing, second dispensing tip 11b is discarded to the not-illustrated discarding port.

Sample dispenser part 10 repeats twice a sample dispensing operation including, as a unit sequence, the attachment of second dispensing tip 11b, the aspiration of the sample, the dispensing of the sample, and the discarding of second dispensing tip 11b. Therefore, every time sample dispenser part 10 performs the dispensing operation via second dispensing tip 11b, sample dispenser part 10 replaces second dispensing tip 11b with unused dispensing tip 11 (unused second dispensing tip 11b). Consequently, it is possible to more surely achieve prevention of contamination.

Second reaction container 71 after the dispensing is taken by reaction-container transfer part 52a and transferred to holding hole 51a positioned in first position 250 of container-holding part 51. After transferring second reaction container 71, reaction-container transfer part 52a transfers used first reaction container 70 after aspiration to the next holding hole 51a being moved to first position 250 of container holding part 51. For this reason, second reaction container 71 and used first reaction container 70 are alternately set in holding holes 51a of container holding part 51. Note that second reaction container 71 may be set in holding hole 51a, for example, with respect to every two first reaction containers 70 or every three first reaction containers 70 rather than being set alternately with first reaction container 70. First reaction container 70 after aspiration is subjected to discarding processing in step S10. Note that first reaction container 70 after aspiration may be transferred on the same route as second reaction container 71 by container holding part 51.

In step S11, the R7 reagent is dispensed into second reaction container 71. When second reaction container 71 is transferred to reagent dispensing position 230 of second reagent dispenser unit 22 by container holding part 51, second reagent dispenser unit 22 dispenses the R7 reagent into second reaction container 71 held by container holding part 51. Consequently, the second solid phasing processing is performed.

In step S12, the third BF separation processing is performed by second separation part 30b. First, when second reaction container 71 is transferred to fifth position 290 by container holding part 51, reaction-container transfer part 52c takes second reaction container 71 and transfers second reaction container 71 to second separation part 30b.

Second separation part 30b performs the third BF separation processing on a specimen in second reaction container 71 and removes a liquid component. When the third BF separation processing ends, reaction-container transfer part 52c transfers second reaction container 71 to sixth position 300.

In step S13, the R8 reagent is dispensed into second reaction container 71. When second reaction container 71 is transferred to sixth position 300, reaction-container transfer part 52d takes second reaction container 71 and transfers second reaction container 71 to dispenser part 24a of fourth reagent dispenser unit 24. Dispenser part 24a dispenses the R8 reagent into second reaction container 71.

In step S14, the R9 reagent is dispensed into second reaction container 71. Reaction-container transfer part 52d transfers second reaction container 71 to dispenser part 24b of fourth reagent dispenser unit 24. Dispenser part 24b dispenses the R9 reagent into second reaction container 71. When the R9 reagent is dispensed, reaction-container transfer part 52d returns second reaction container 71 to container holding part 51.

In step S15, measurement processing of immune complex 85 is performed. When second reaction container 71 is transferred to a predetermined take-out position by container holding part 51, reaction-container transfer part 52e takes second reaction container 71 and transfers second reaction container 71 to measurement part 40. The measurement processing is executed by measurement part 40. The intensity of light generated by causing a substrate to react to a label is measured. A measurement result of measurement part 40 is output to controller 104. The processing performed in the fourth rotation of container holding part 51 in steps S9 to S15 is completed.

After the measurement ends, in step S16, reaction-container transfer part 52e takes second reaction container 71 after measurement from measurement part 40 and discards second reaction container 71 to discarding port 114. Note that, in container holding part 51, used first reaction container 70 after aspiration in step S9 may be set in the next holding hole 51a of holding hole 51a in which second reaction container 71 is set. In this case, used first reaction container 70 is transferred to a take-out position of reaction-container transfer part 52e while being held by container holding part 51 without being transferred to second separation part 30b and fourth reagent dispenser unit 24. Reaction-container transfer part 52e takes used first reaction container 70 transferred to the take-out position by container holding part 51 and discards first reaction container 70 to discarding port 114.

The measurement processing operation by the first test processing of immunoassay apparatus 100 is performed as explained above.

(Overview of the Immunoassay by the Second Test Processing)

Figure 8:
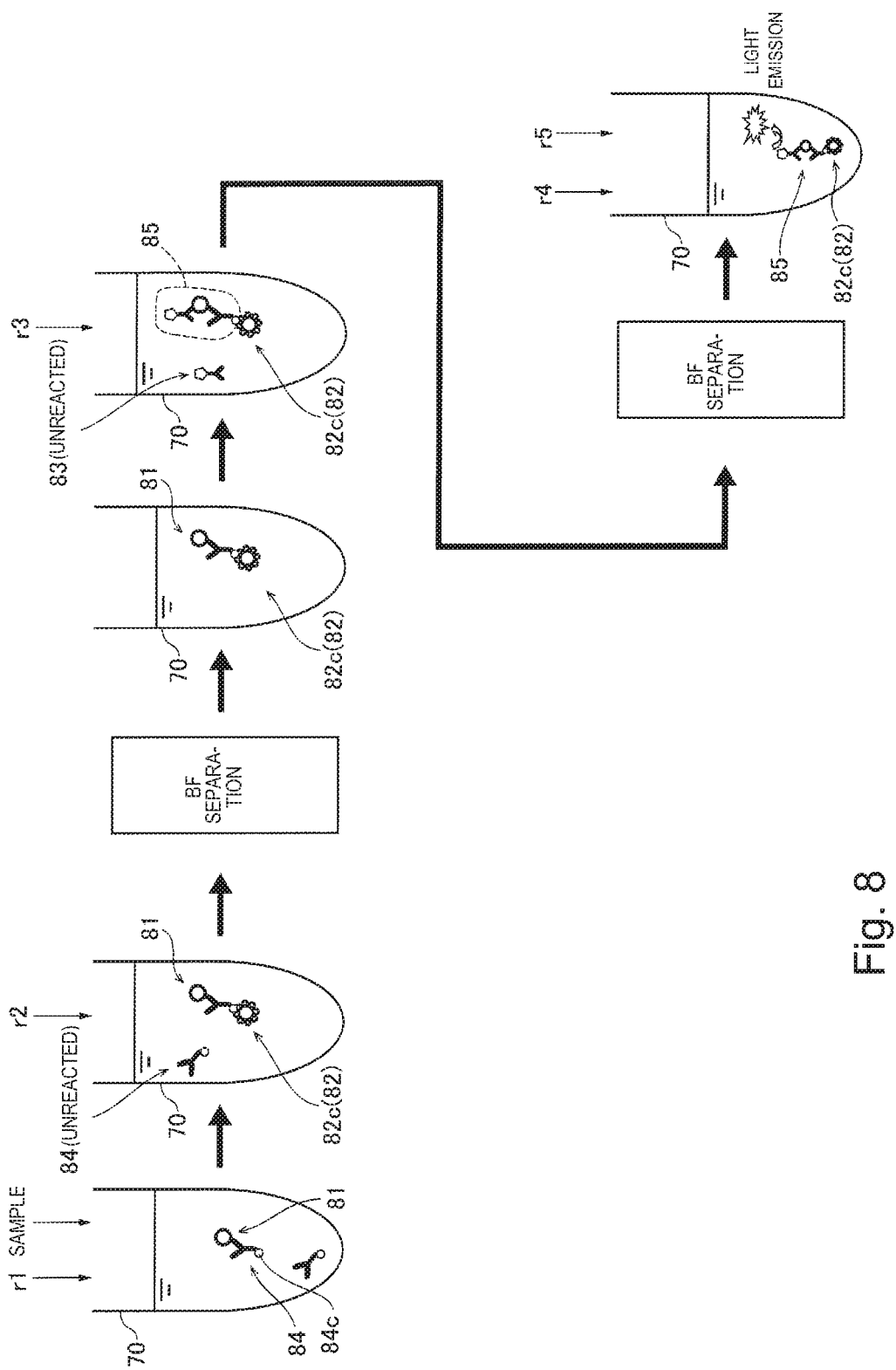
FIG. 8 is a diagram illustrating an overview of immunoassay by second test processing of an immunoassay apparatus illustrated in FIG. 2.

In the configuration example shown in FIG. 2, as illustrated in FIG. 8, the immunoassay is performed using the r1 reagent to the r5 reagent. In an example illustrated in FIG. 8, the second test processing of performing the immune chemical measurement in which the immune complex transfer method is not carried out is explained. Target substance 81 tested by the second test processing is measured at sufficient accuracy even if the first test processing is not performed. Since a test is performed by the second test processing, it is possible to reduce a test time compared with the first test processing.

First, a sample including target substance 81 and the r1 reagent are dispensed into first reaction container 70. The r1 reagent contains capturing substance 84 and reacts with target substance 81 to be bound with target substance 81. Capturing substance 84 includes binding substance 84c for capturing substance 84 to be bound with third solid-phase carrier 82c. Note that the r1 reagent may be the same reagent as the R4 reagent.

For the binding of the binding substance and the solid-phase carrier, combinations can be used, such as biotin and avidins, hapten and an anti-hapten antibody, nickel and a histidine tag, and glutathione and glutathione-S-transferase.

For example, capturing substance 84 is an antibody modified by biotin (a biotin antibody). That is, in capturing substance 84, biotin is modified as binding substance 84c.

Subsequently, the r2 reagent is dispensed into first reaction container 70. The r2 reagent contains third solid-phase carrier 82c as solid-phase carrier 82. Third solid-phase carrier 82c is bound with binding substance 84c of capturing substance 84. Third solid-phase carrier 82c is a magnetic particle to which streptavidin that can bind with biotin is fixed (a StAvi-bound magnetic particle). The streptavidin of the StAvi-bound magnetic particle reacts with biotin, which is third binding substance 84c, to be bound with the biotin. As a result, target substance 81 and capturing substance 84 are bound with third solid-phase carrier 82c. Note that third solid-phase carrier 82c may include the same components as the components of second solid-phase carrier 82b used in the first test processing. That is, the r2 reagent may be the same reagent as the R7 reagent. In this case, a common reagent can be used as a reagent containing second solid-phase carrier 82b and a reagent containing third solid-phase carrier 82c. Therefore, it is possible to prevent types of reagents disposed in immunoassay apparatus 100 from increasing.

Target substance 81 and capturing substance 84 formed on third solid-phase carrier 82c and unreacted capturing substance 84 are separated by the primary BF separation processing. Unnecessary components such as unreacted capturing substance 84 are removed from first reaction container 70 by the primary BF separation processing.

Subsequently, the r3 reagent is dispensed into first reaction container 70. The r3 reagent contains labeled substance 83 that reacts with target substance 81 to be bound with target substance 81. As a result, immune complex 85 including target substance 81, labeled substance 83, and capturing substance 84 is formed on third solid-phase carrier 82c. In the example illustrated in FIG. 8, labeled substance 83 is an ALP (alkaline phosphatase) labeled antibody. Note that the r3 reagent may be the same reagent as the R3 reagent.

Immune complex 85 formed on third solid-phase carrier 82c and unreacted labeled substance 83 are separated by the secondary BF separation processing. Unnecessary components such as unreacted labeled substance 83 are removed from first reaction container 70 by the secondary BF separation processing.

Thereafter, the r4 reagent and the r5 reagent are dispensed into first reaction container 70. The r4 reagent contains a buffer solution. Immune complex 85 bound with third solid-phase carrier 82c is dispersed in the buffer solution. The r5 reagent contains a chemical light emitting substrate. The buffer liquid contained in the r4 reagent has a composition for facilitating a reaction between a label (an enzyme) of labeled substance 83 included in immune complex 85 and a substrate. Light is generated by causing the substrate to react with the label. The intensity of the generated light is measured by measurement part 40. Note that the r4 reagent and the r5 reagent may be the same reagents as the R8 reagent and the R9 reagent, respectively.

(Explanation of an Immunoassay Processing Operation by the Second Test Processing)

Figure 9:
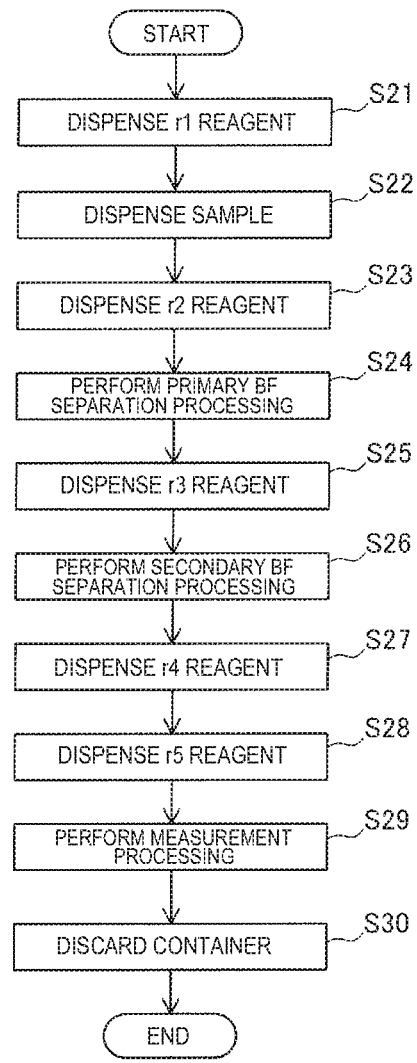
FIG. 9 is a flowchart illustrating a measurement processing operation by second test processing of an immunoassay apparatus according to an embodiment.

A measurement processing operation of immunoassay apparatus 100 illustrated in FIG. 2 is explained with reference to FIG. 9. In an example illustrated in FIG. 9, second test processing of performing immunoassay, in which the immune complex transfer method is not carried out, is explained. In the following explanation, FIG. 9 is referred to concerning steps of the measurement processing operation. FIG. 2 is referred to concerning the parts of immunoassay apparatus 100.

In the measurement, container holding part 51 rotates by a unit pitch clockwise (in an A1 direction) at every predetermined time interval. Reaction-container transfer part 52 performs container transfer between container holding part 51 and sample dispenser part 10, reagent dispenser part 20, and BF separation part 30 according to timings of the processes in sample dispenser part 10, reagent dispenser part 20, and BF separation part 30. When focusing on measurement of one sample, in this embodiment, container holding part 51 rotates once from the dispensing of the sample until the sample is transferred to measurement part 40.

In step S21, the r1 reagent is dispensed into first reaction container 70. First, first reaction container 70 is supplied from container supply part 112 to reaction-container holding part 60. First reagent dispenser unit 21 dispenses the r1 reagent into first reaction container 70 held by reaction-container holding part 60.

In step S22, a sample is dispensed into first reaction container 70. Dispensing tip 11 is attached to sample dispenser part 10 in tip attachment position 220. Sample dispenser part 10 aspirates the sample in sample aspiration position 210. Sample dispenser part 10 dispenses the aspirated sample into first reaction container 70 held by reaction-container holding part 60. After the dispensing, dispensing tip 11 is discarded to the not-illustrated discarding port. Every time sample dispenser part 10 performs a dispensing operation via dispensing tip 11, sample dispenser part 10 replaces dispensing tip 11 with unused dispensing tip 11.

After the dispensing of the sample, reaction-container transfer part 52a transfers first reaction container 70 to holding hole 51a positioned in the first position 250 of container holding part 51.

In step S23, the r2 reagent is dispensed into first reaction container 70. When first reaction container 70 is transferred to reagent dispensing position 230 of second reagent dispenser unit 22 by container holding part 51, second reagent dispenser unit 22 dispenses the r2 reagent into first reaction container 70 held by container holding part 51.

In step S24, the primary BF separation processing is performed by first separation part 30a. First, when first reaction container 70 is transferred to second position 260 by container-holding part 51, reaction-container transfer part 52b takes first reaction container 70 and transfers first reaction container 70 to first separation part 30a.

First separation part 30a performs the primary BF separation processing on a specimen in first reaction container 70 and removes a liquid component. When the primary BF separation processing ends, reaction-container transfer part 52b sets first reaction container 70 in holding hole 51a positioned in third position 270 of container holding part 51.

In step S25, the r3 reagent is dispensed into first reaction container 70. When first reaction container 70 is transferred to reagent dispensing position 240 of third reagent dispenser unit 23 by container holding part 51, third reagent dispenser unit 23 dispenses the r3 reagent into first reaction container 70 held by container holding part 51.

In step S26, the secondary BF separation processing is performed by second separation part 30b. First, when first reaction container 70 is transferred to fifth position 290 by container holding part 51, reaction-container transfer part 52c takes first reaction container 70 and transfers first reaction container 70 to second separation part 30b.

Second separation part 30b performs the secondary BF separation processing on a sample in first reaction container 70 and removes a liquid component. When the secondary BF separation processing ends, reaction-container transfer part 52c transfers first reaction container 70 to sixth position 300.

In step S27, the r4 reagent is dispensed into first reaction container 70. When first reaction container 70 is transferred to sixth position 300, reaction-container transfer part 52d takes first reaction container 70 and transfers first reaction container 70 to dispenser part 24a of fourth reagent dispenser unit 24. Dispenser part 24a dispenses the r4 reagent into first reaction container 70.

In step S28, the r5 reagent is dispensed into first reaction container 70. Reaction-container transfer part 52d transfers first reaction container 70 to dispenser part 24b of fourth reagent dispenser unit 24. Dispenser part 24b dispenses the r5 reagent into first reaction container 70. When the r5 reagent is dispensed, reaction-container transfer part 52d returns first reaction container 70 to container holding part 51.

In step S29, measurement processing of immune complex 85 is performed. When first reaction container 70 is transferred to a predetermined take-out position by container holding part 51, reaction-container transfer part 52e takes first reaction container 70 and transfers first reaction container 70 to measurement part 40. The measurement processing is executed by measurement part 40. The intensity of light generated by causing a substrate to react to a label is measured. A measurement result of measurement part 40 is output to controller 104.

After the measurement ends, in step S30, reaction-container transfer part 52e takes first reaction container 70 after measurement from measurement part 40 and discards first reaction container 70 in discarding port 114.

The measurement processing operation by the second test processing of immunoassay apparatus 100 is performed as explained above.

(Overview of Control of the First Test Processing and the Second Test Processing)

Figure 10:
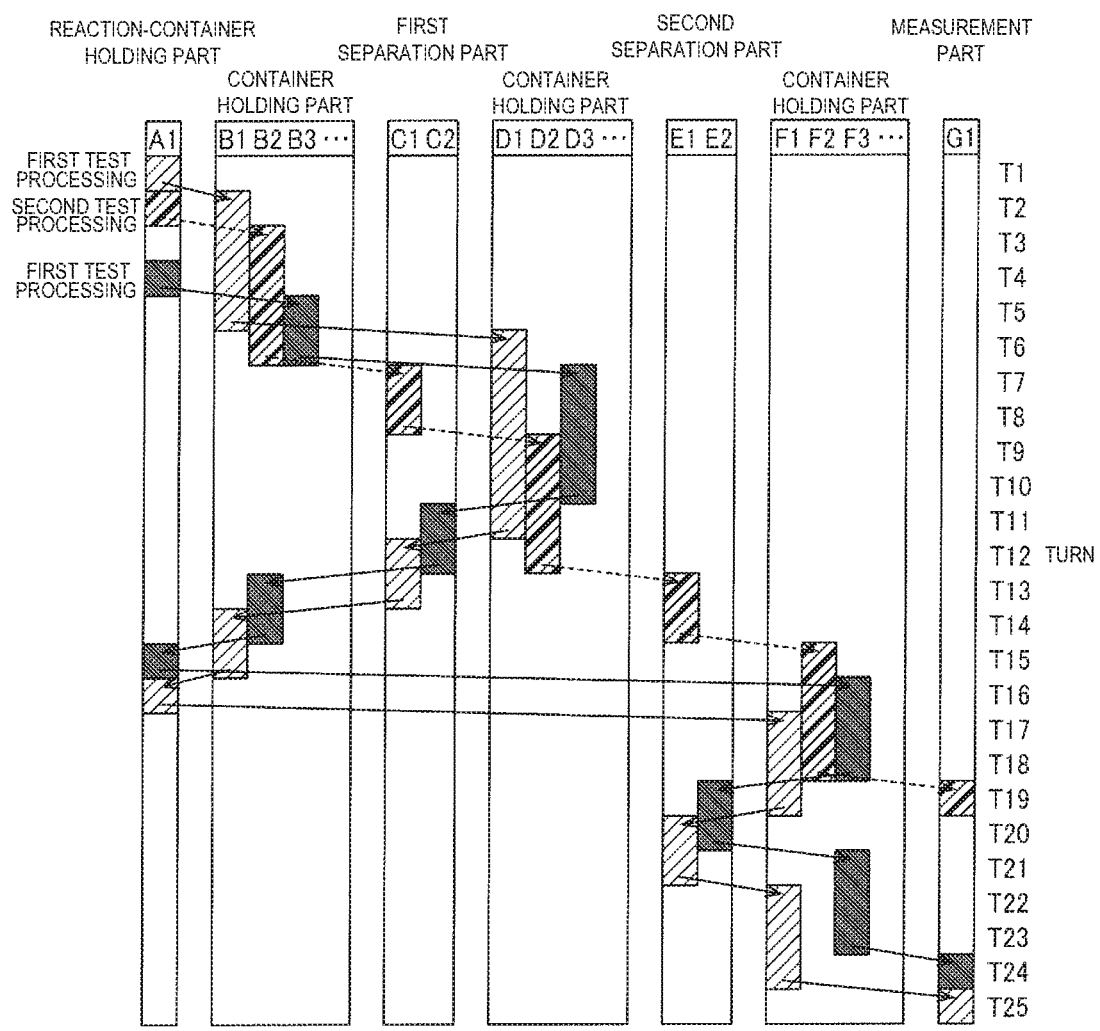
FIG. 10 is a diagram illustrating an overview of control of first test processing and second test processing of an immunoassay apparatus according to an embodiment.

In the configuration example illustrated in FIG. 2, as in an example illustrated in FIG. 10, the first test processing and the second test processing may be performed concurrently. In the example illustrated in FIG. 10, test processing for two measurement orders of the first test processing and one measurement order of the second test processing is explained.

In the first test processing that starts from reaction-container holding part 60 in turn T1, a target container is disposed in hole B1 of container holding part 51, and the reaction processing is performed in turns T2 to T5. Thereafter, in turns T6 to T11, the target container is disposed in hole D1 of container holding part 51, and the reaction processing is performed. In turns T12 to T13, the target container is disposed in hole C1 of first separation part 30a, and the BF separation processing is performed. In turns T14 to T15, the target container is disposed in hole B1 of container holding part 51, and the reaction processing is performed. In turn T16, the target container is disposed in hole A1 of reaction-container holding part 60, and the dispensing processing is performed. In turns T17 to T19, a target container is disposed in hole F1 of container holding part 51, and the reaction processing is performed. In turns T20 to T21, the target container is disposed in hole E1 of second separation part 30b, and the BF separation processing is performed. In turns T22 to T24, the target container is disposed in a hole F1 of container holding part 51, and the reaction processing is performed. In turn T25, the target container is disposed in hole G1 of measurement part 40, and the measurement processing is performed.

In the second test processing that starts from reaction-container holding part 60 in turn T2, a target container is disposed in hole B2 of container holding part 51, and the reaction processing is performed in turns T3 to T6. Thereafter, in turns T7 to T8, the target container is disposed in hole C1 of first separation part 30a, and the BF separation processing is performed. In turns T9 to T12, the target container is disposed in hole D1 of container holding part 51, and the reaction processing is performed. In turns T13 to T14, the target container is disposed in hole E1 of second separation part 30b, and the BF separation processing is performed. In turns T15 to T18, the target container is disposed in hole F2 of container holding part 51, and the reaction processing is performed. In turn T19, the target container is disposed in hole G1 of measurement part 40, and the measurement processing is performed.

In the first test processing that starts from reaction-container holding part 60 in turn T4, a target container is disposed in hole B3 of container holding part 51, and the reaction processing is performed in turns T5 to T6. Thereafter, in turns T7 to T10, the target container is disposed in hole D3 of container holding part 51, and the reaction processing is performed. In turns T11 to T12, the target container is disposed in hole C2 of first separation part 30a, and the BF separation processing is performed. In turns T13 to T14, the target container is disposed in hole B2 of container holding part 51, and the reaction processing is performed. In turn T15, the target container is disposed in hole A1 of reaction-container holding part 60, and the dispensing processing is performed. In turns T16 to T18, a target container is disposed in hole F3 of container holding part 51, and the reaction processing is performed. In turns T19 to T20, the target container is disposed in hole E2 of second separation part 30b, and the BF separation processing is performed. In turns T21 to T23, the target container is disposed in hole F3 of container holding part 51, and the reaction processing is performed. In turn T24, the target container is disposed in hole G1 of measurement part 40, and the measurement processing is performed.

Note that the first test processing and the second test processing may be selected by a user, may be selected according to target substance 81 to be measured, or may be selected according to measurement items. The measurement items include measurement items such as an HIV antibody, an HA antibody, an HBs antibody, an HBc antibody, an HCV antibody, and syphilis antibody. In this case, in a condition in which a specific measurement item is selected by the user, the first test processing of performing the high-sensitivity immunoassay in which the immune complex transfer method is used may be performed.

(Overview of Control of First Test Processing)

Figure 11:
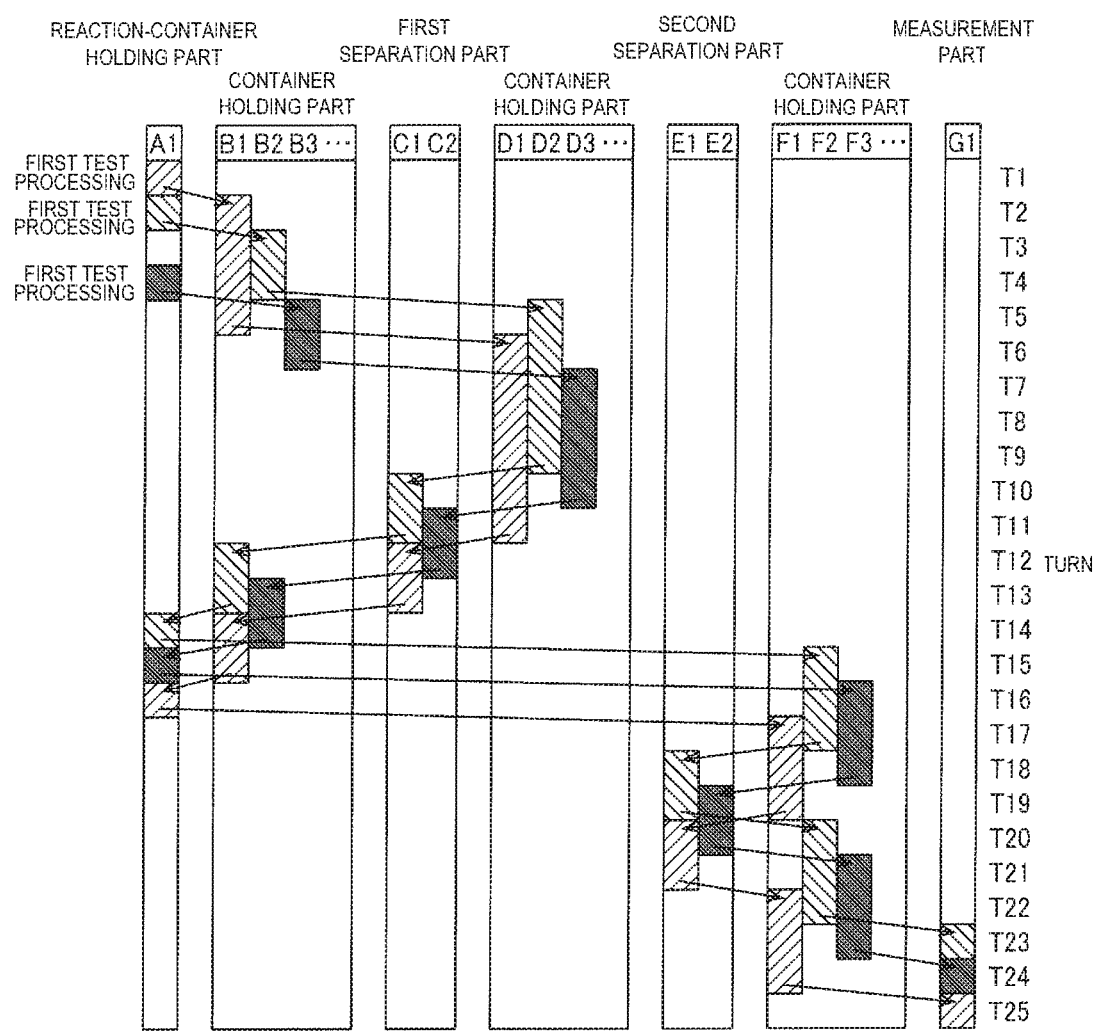
FIG. 11 is a diagram illustrating an overview of control of first test processing of an immunoassay apparatus according to an embodiment.

In the configuration example illustrated in FIG. 2, as in an example illustrated in FIG. 11, multiple measurements with first test processing may be performed. In the example illustrated in FIG. 11, test processing for three measurement orders of first test processing is explained.

In the first test processing that starts from reaction-container holding part 60 in turn T1, a target container is disposed in hole B1 of container holding part 51, and the reaction processing is performed in turns T2 to T5. Thereafter, in turns T6 to T11, the target container is disposed in hole D1 of container holding part 51, and the reaction processing is performed. In turns T12 to T13, the target container is disposed in hole C1 of first separation part 30a, and the BF separation processing is performed. In turns T14 to T15, the target container is disposed in hole B1 of container holding part 51, and the reaction processing is performed. In turn T16, the target container is disposed in hole A1 of reaction-container holding part 60, and the dispensing processing is performed. In turns T17 to T19, a target container is disposed in hole F1 of container holding part 51, and the reaction processing is performed. In turns T20 to T21, the target container is disposed in hole E1 of second separation part 30b, and the BF separation processing is performed. In turns T22 to T24, the target container is disposed in hole F1 of container holding part 51, and the reaction processing is performed. In turn T25, the target container is disposed in hole G1 of measurement part 40, and the measurement processing is performed.

In the first test processing that starts from reaction-container holding part 60 in turn T2, a target container is disposed in hole B2 of container holding part 51, and the reaction processing is performed in turns T3 to T4. Thereafter, in turns T4 to T9, the target container is disposed in hole D2 of container holding part 51, and the reaction processing is performed. In turns T10 to T11, the target container is disposed in hole C1 of first separation part 30a, and the BF separation processing is performed. In turns T12 to T13, the target container is disposed in hole B1 of container holding part 51, and the reaction processing is performed. In turn T14, the target container is disposed in hole A1 of reaction-container holding part 60, and the dispensing processing is performed. In turns T15 to T17, a target container is disposed in hole F2 of container holding part 51, and the reaction processing is performed. In turns T18 to T19, the target container is disposed in hole E1 of second separation part 30b, and the BF separation processing is performed. In turns T20 to T22, the target container is disposed in hole F2 of container holding part 51, and the reaction processing is performed. In turn T23, the target container is disposed in hole G1 of measurement part 40, and the measurement processing is performed.

In the first test processing that starts from reaction-container holding part 60 in turn T4, a target container is disposed in hole B3 of container holding part 51, and the reaction processing is performed in turns T5 to T6. Thereafter, in turns T7 to T10, the target container is disposed in hole D3 of container holding part 51, and the reaction processing is performed. In turns T11 to T12, the target container is disposed in hole C2 of first separation part 30a, and the BF separation processing is performed. In turns T13 to T14, the target container is disposed in hole B2 of container holding part 51, and the reaction processing is performed. In turn T15, the target container is disposed in hole A1 of reaction-container holding part 60, and the dispensing processing is performed. In turns T16 to T18, a target container is disposed in hole F3 of container holding part 51, and the reaction processing is performed. In turns T19 to T20, the target container is disposed in hole 2E of second separation part 30b, and the BF separation processing is performed. In turns T21 to T23, the target container is disposed in hole F3 of container holding part 51, and the reaction processing is performed. In turn T24, the target container is disposed in hole G1 of measurement part 40, and the measurement processing is performed.

(Overview of Control of Second Test Processing)

Figure 12:
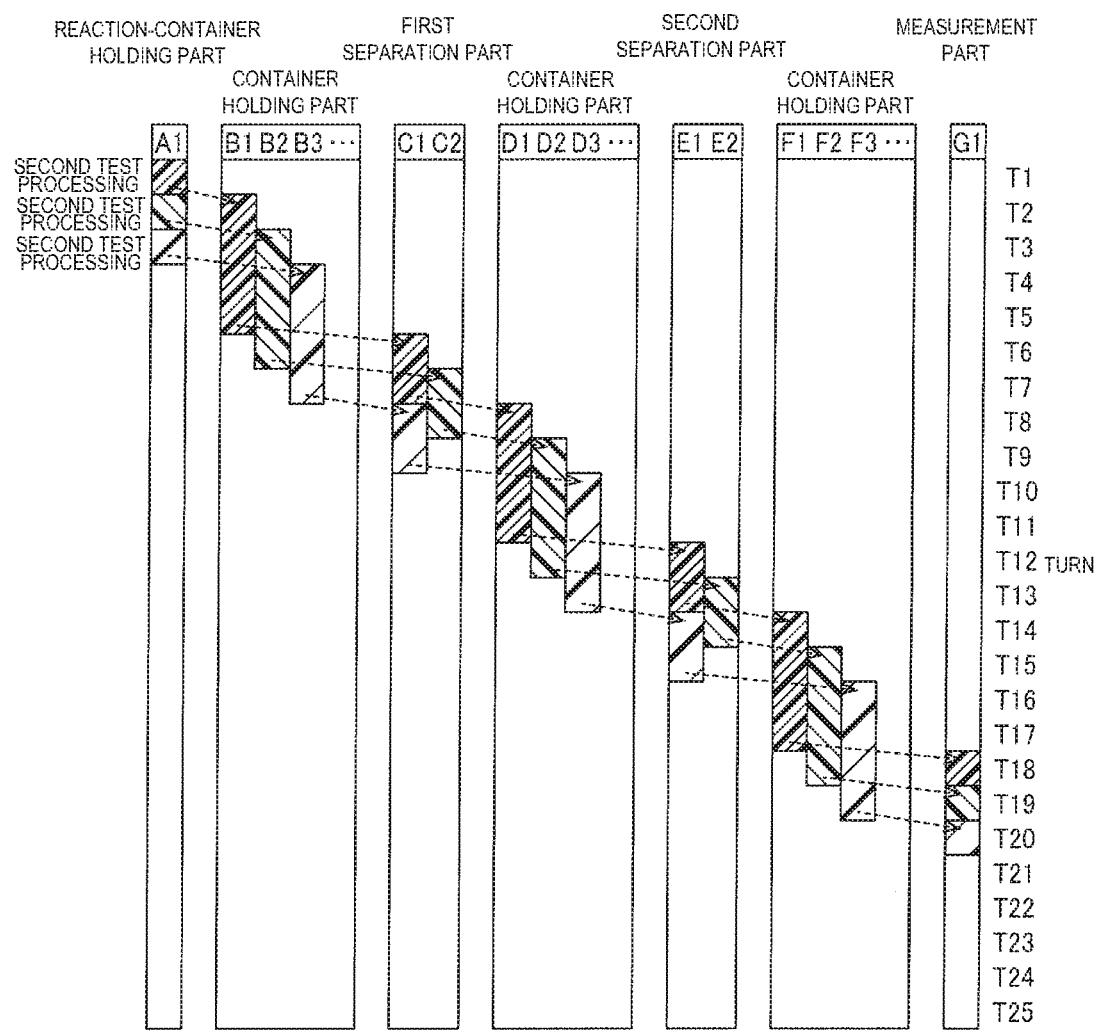
FIG. 12 is a diagram illustrating an overview of control of second test processing of an immunoassay apparatus according to an embodiment.

In the configuration example illustrated in FIG. 2, as in an example illustrated in FIG. 12, multiple measurements with second test processing may be performed. In the example illustrated in FIG. 12, test processing for three measurement orders of second test processing is explained.

In the second test processing that starts from reaction-container holding part 60 in turn T1, a target container is disposed in hole B1 of container holding part 51, and the reaction processing is performed in turns T2 to T5. Thereafter, in turns T6 to T7, the target container is disposed in hole C1 of first separation part 30a, and the BF separation processing is performed. In turns T8 to T11, the target container is disposed in hole D1 of container holding part 51, and the reaction processing is performed. In turns T12 to T13, the target container is disposed in hole E1 of second separation part 30b, and the BF separation processing is performed. In turns T14 to T17, the target container is disposed in hole F1 of container holding part 51, and the reaction processing is performed. In turn T18, the target container is disposed in hole G1 of measurement part 40, and the measurement processing is performed.

In the second test processing that starts from reaction-container holding part 60 in turn T2, a target container is disposed in hole B2 of container holding part 51, and the reaction processing is performed in turns T3 and T6. Thereafter, in turns T7 to T8, the target container is disposed in hole C2 of first separation part 30a, and the BF separation processing is performed. In turns T9 to T12, the target container is disposed in hole D2 of container holding part 51, and the reaction processing is performed. In turns T13 to T14, the target container is disposed in hole E2 of second separation part 30b, and the BF separation processing is performed. In turns T15 to T18, the target container is disposed in hole F2 of container holding part 51, and the reaction processing is performed. In turn T19, the target container is disposed in hole G1 of measurement part 40, and the measurement processing is performed.

In the second test processing that starts from reaction-container holding part 60 in turn T3, a target container is disposed in hole B3 of container holding part 51, and the reaction processing is performed in turns T4 to T7. Thereafter, in turns T8 to T9, the target container is disposed in hole C1 of first separation part 30a, and the BF separation processing is performed. In turns T10 to T13, the target container is disposed in hole D3 of container holding part 51, and the reaction processing is performed. In turns T14 to T15, the target container is disposed in hole E1 of second separation part 30b, and the BF separation processing is performed. In turns T16 to T19, the target container is disposed in hole F3 of container holding part 51, and the reaction processing is performed. In turn T20, the target container is disposed in hole G1 of measurement part 40, and the measurement processing is performed.

[Modifications]

Note that the embodiments disclosed herein should be considered illustrative and not restrictive in all aspects. The scope of the present invention is indicated by the scope of claims rather than the above explanation of the embodiments and includes all changes (modifications) within meanings and scopes equivalent to the scope of the claims.

Figure 13:
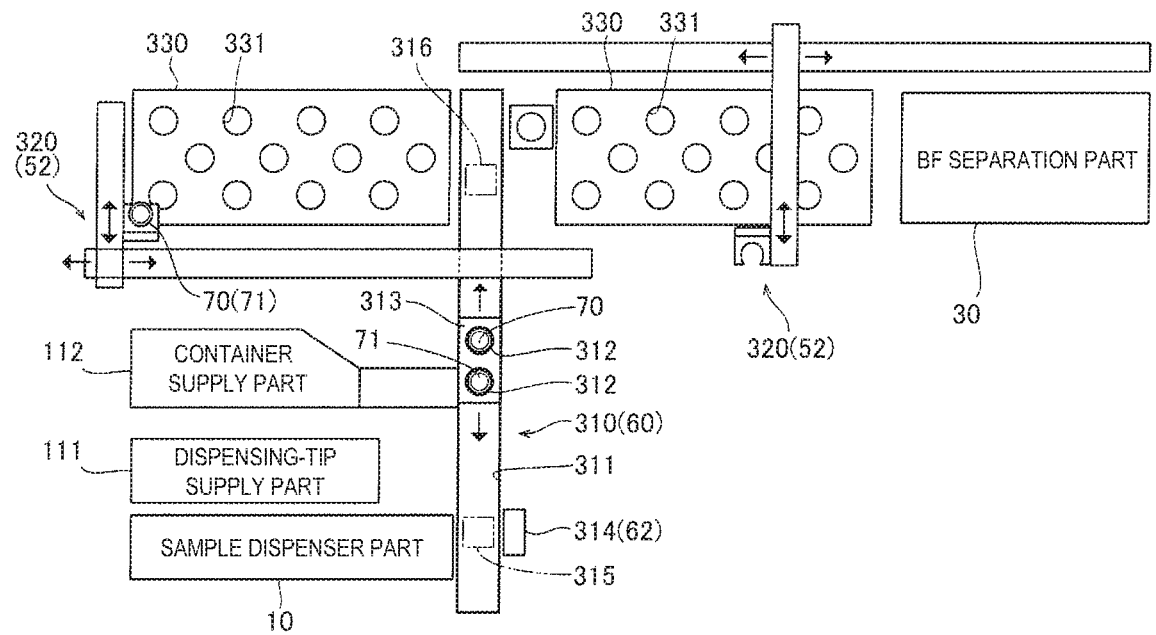
FIG. 13 is a schematic plan view illustrating a modification of a reactor-container holding part.

For example, a modification illustrated in FIG. 13 may be adopted as another configuration example of reaction-container holding part 60 and container holding part 51.

In this modification, reaction-container holding part 310 movable between sample dispensing position 315 and container delivery position 316 is provided. Reaction-container holding part 310 is configured to linearly move holding member 313 including holding hole 312 along linear conveyance path 311. A plurality of holding holes 312 are provided. In FIG. 13, an example is illustrated in which two holding holes 312 are provided. First reaction container 70 and second reaction container 71 supplied from container supply part 112 can be set in holding holes 312. In a case where the magnetic particle is used as solid-phase carrier 82, second magnetism collection part 314 may be provided in reaction-container holding part 310. Second magnetism collection part 314 is disposed, for example, in a side position or a lower position of conveyance path 310 in the vicinity of sample dispensing position 315. Second magnetism collection part 314 may be attached to holding member 313.

Reaction-container holding part 310 can move holding member 313 to dispose first reaction container 70 and second reaction container 71 in sample dispensing position 315. Sample dispenser part 10 aspirates, via second dispensing tip 11b, immune complex 85 released from solid-phase carrier 82 by releasing reagent 86 via first dispensing tip 11a supplied from dispensing-tip supply part 111. Sample dispenser part 10 dispenses, into second reaction container 71, immune complex 85 aspirated via second dispensing tip 11b.

In a configuration example illustrated in FIG. 13, reaction parts 330 including holding holes 331 are provided instead of container holding part 51. Reaction-container transfer part 320 takes first reaction container 70 and second reaction container 71 from holding member 313 in container delivery position 316 and sets first reaction container 70 and second reaction container 71 in reaction part 330. Reaction-container transfer part 320 transfers first reaction containers 70 and second reaction containers 71 one by one between reaction parts 330 and BF separation parts 30. Note that reaction part 330 may have a function of warming or maintaining first reaction container 70 and second reaction container 71 held by holding hole 331 to a predetermined temperature. In this case, reaction part 330 may be capable of changing temperature setting. The configuration explained above may be adopted.

In the configuration example illustrated in FIG. 2, the example is illustrated in which sample dispenser part 10 dispenses, into second reaction container 71, immune complex 85 released from solid-phase carrier 82a by releasing reagent 86. However, not only this, but immune complex 85 released from solid-phase carrier 82a by releasing reagent 86 may be dispensed into second reaction container 71 by a dispenser part other than sample dispenser part 10.

In the configuration example illustrated in FIG. 2, the example in FIG. 7 is illustrated in which container holding part 51 makes four rotations to perform the sample measurement. However, not only this, but measurement of one sample may be completed in the number of rotations other than four. In this case, for example, reagent dispenser part 20 may include four or more reagent dispenser units.

In the configuration example illustrated in FIG. 2, the example is illustrated as non-limiting example in which the first test processing and the second test processing are performed concurrently. Instead, a first test mode of performing the first test processing and a second test mode of performing the second test processing may be switched. That is, controller 104 may switch the first test mode of controlling the first test processing and the second test mode of controlling the second test processing. Controller 104 may switch the first test mode of measuring a signal based on a label included in an immune complex stored in second reaction container 71 and the second test mode of measuring a signal based on a label included in an immune complex stored in first reaction container 70. In this case, one or more measurements only in the first test processing are performed in the first test mode, whereas one or more measurements only in the second test processing are performed in the second test mode. Consequently, in the case of performing the first test processing, immunoassay apparatus 100 is switched to the first test mode to optimize its operation for the first test processing. Therefore, it is possible to efficiently perform the first test processing. In the case of performing the second test processing is performed, immunoassay apparatus 100 is switched to second test mode to optimize its operation for the second test processing. Therefore, it is possible to efficiently perform the second test processing.

The switching of the first test mode and the second test mode may be performed by restarting immunoassay apparatus 100 based on operation by the user. That is, controller 104 may switch the first test mode and the second test mode according to the selection by the user. Consequently, it is possible to easily perform a test by the first test processing or the second test processing desired by the user. Controller 104 may switch the first test mode and the second test mode by restarting immunoassay apparatus 100. Consequently, by restarting immunoassay apparatus 100 during the mode switching, it is possible to stably shift to the first test mode of the second test mode.

The first test mode and the second test mode may be switched according to measurement items. That is, controller 104 may switch the first test mode and the second test mode according to the measurement items. Consequently, it is possible to efficiently perform a test according to a test mode suitable for the measurement items. The measurement items include measurement items such as HIV antibody, an HA antibody, an HBs antibody, an HBc antibody, an HCV antibody, and syphilis antibody. In the case of measurement items that require more accuracy, controller 104 may switch the test mode to the first test mode.

Figure 14:
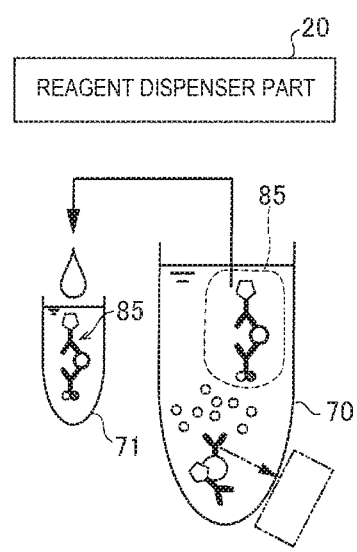
FIG. 14 is a schematic diagram illustrating a modification of dispense processing into a second reaction container of an immune complex.

In the configuration example illustrated in FIG. 2, the example is illustrated in which the immune complex released from the solid-phase carrier by the releasing reagent is dispensed into the second reaction container. However, not only this, but as in a modification illustrated in FIG. 14, immune complex 85 released from the solid-phase carrier by the releasing reagent may be dispensed into second reaction container 71 by reagent dispenser part 20. Consequently, it is possible to dispense immune complex 85 for the immune complex transfer method with reagent dispenser part 20 for dispensing a reagent.

Figure 15:
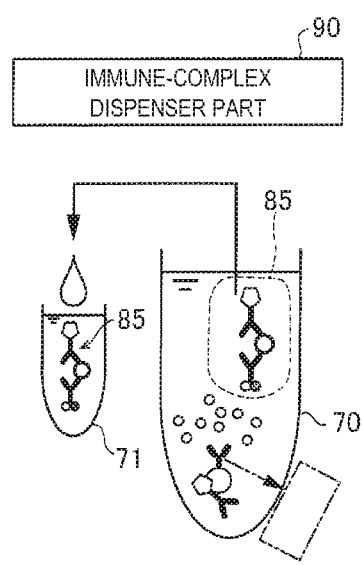
FIG. 15 is a schematic diagram illustrating another modification of dispense processing into a second reaction container of an immune complex.

As in a modification illustrated in FIG. 15, immune-complex dispenser part 90 for dispensing released immune complex 85 may be provided. Immune complex 85 released from the solid-phase carrier by the releasing reagent may be dispensed into second reaction container 71 by immune-complex dispenser part 90. Consequently, immune complex 85 for the immune complex transfer method can be dispensed by immune-complex dispenser part 90 optimized to dispense an immune complex. Therefore, it is possible to efficiently perform the dispensing of immune complex 85.

The invention claimed is:

1. An immunoassay method comprising:
controlling an immunoassay apparatus to:
aspirate a sample containing a target substance in a sample container and dispense the sample in a first reaction container;
dispense, in the first reaction container, (A) a first reagent including a solid phase carrier, (B) a second reagent including a labeling substance and (C) a third reagent to release an immune-complex having the target substance and the labeling substance from the solid phase carrier, to produce a mixture containing the solid phase carrier and the immune-complex released by the third reagent from the solid phase carrier;
aspirate a part of the mixture in the first reaction container and dispense the part of the mixture in a second reaction container that is different from the first reaction container; and
detect a signal derived from the labeling substance in the second reaction container.

2. The immunoassay method of claim 1, further comprising
controlling the immunoassay apparatus to:
supply, before dispensing the reagents (A), (B) and (C) in the first reaction container, the first reaction container to a sample dispensing position where a pipette of a sample dispenser of the immunoassay apparatus dispenses the sample;
remove the first reaction container in which the reagents (A), (B) and (C) have been dispensed, from the sample dispensing position, and
supply the second reaction container to the sample dispensing position, after removing the first reaction container.

3. The immunoassay method of claim 2, further comprising
controlling the immunoassay apparatus to:
transfer the first reaction container in which the sample has been dispensed to a terminal position where the pipette of the sample dispenser aspirates the part of the mixture in the first reaction container, through one or more positions where one or more reagent dispensers dispense reagents (A), (B) and (C) in the first reaction container in dispensing the reagents (A), (B) and (C) in the first reaction container.

4. The immunoassay method of claim 3, further comprising
controlling the immunoassay apparatus to:
transfer the second reaction container to a detecting position where a detector of the immunoassay apparatus detects the signal derived from the labeling substance in the second reaction container.

5. The immunoassay method of claim 3, wherein dispensing the part of the mixture into the second reaction container comprises dispensing the part of the mixture into the second reaction container using the sample dispenser.

6. The immunoassay method of claim 1, further comprising controlling the immunoassay apparatus to:

attach a first dispensing tip to a sample dispenser of the immunoassay apparatus before dispensing the sample into the first reaction container, so that dispensing the sample into the first reaction container comprises dispensing the sample into the first reaction container through the first dispensing tip by the sample dispenser, detach the first dispensing tip from the sample dispenser after dispensing the sample into the first reaction container; and attach a second dispensing tip to the sample dispenser after detaching the first dispensing tip from the sample dispenser and before dispensing the part of the mixture in the first reaction container to the second reaction container, so that dispensing the part of the mixture in the first reaction container to the second reaction container comprises dispensing the part of the mixture in the first reaction container to the second reaction container through the second dispensing tip by the sample dispenser.

7. The immunoassay method of claim 1, further comprising controlling the immunoassay apparatus to:

remove an unreacted substance, not bound to an immune complex of the target substance and the solid phase carrier, from a mixture of the reagents (A) and (B) or the mixture containing the solid phase carrier and the immune-complex released by the third reagent from the solid phase carrier, while applying magnetic force to the first reaction container such that the solid phase carrier is drawn to an inner side of the first reaction container.

8. The immunoassay method of claim 7, further comprising controlling the immunoassay apparatus to:

after removing the unreacted substance, wash the immune complex in the first reaction container by supplying washing solution in the first reaction container and aspirating the washing solution from the first reaction container.

9. The immunoassay method of claim 7, wherein removing the unreacted substance from the first reaction container is performed after the reagents (A) and (B) are dispensed and before the reagent (C) is dispensed to the first reaction container in dispensing the reagents (A), (B) and (C) in the first reaction container.

* * * * *